United States Patent
Shieh et al.

(10) Patent No.: US 8,405,510 B2
(45) Date of Patent: Mar. 26, 2013

(54) SYSTEM FOR MEASURING BODY BALANCE SIGNALS AND A METHOD FOR ANALYZING THE SAME

(75) Inventors: Jiann-Shing Shieh, Taipei (TW); Chun-Yi Liu, Zhongli (TW); Jia-Rong Yeh, Lontan Township, Taoyuan County (TW); Pei-De Su, Tainan (TW)

(73) Assignee: Yuan Ze University, Jhongli, Taoyuan County (TW)

( * ) Notice: Subject to any disclaimer, the term of this patent is extended or adjusted under 35 U.S.C. 154(b) by 306 days.

(21) Appl. No.: 12/842,747

(22) Filed: Jul. 23, 2010

(65) Prior Publication Data

US 2011/0175736 A1 Jul. 21, 2011

(30) Foreign Application Priority Data

Jan. 20, 2010 (TW) ................ 99101439 A

(51) Int. Cl.
*G08B 23/00* (2006.01)

(52) U.S. Cl. ............... 340/573.1; 340/573.4; 340/407.1; 340/539.12; 340/539.13; 600/552; 600/587; 600/592; 600/595

(58) Field of Classification Search ............... 340/573.1, 340/573.4, 407.1, 539.12, 539.13; 600/552, 600/587, 592, 595
See application file for complete search history.

(56) References Cited

U.S. PATENT DOCUMENTS

| | | | |
|---|---|---|---|
| 5,388,591 A * | 2/1995 | De Luca et al. ............... 600/592 |
| 5,627,327 A | 5/1997 | Zanakis | |
| 5,830,158 A | 11/1998 | Zanakis | |
| 5,919,149 A | 7/1999 | Allum | |
| 6,063,046 A | 5/2000 | Allum | |
| 6,237,256 B1 | 5/2001 | Maki et al. | |
| 6,383,150 B1 * | 5/2002 | Stewart et al. ................ 600/595 |
| 6,561,991 B2 | 5/2003 | McLeod et al. | |
| 6,602,210 B2 * | 8/2003 | Savet ............................ 600/595 |
| 6,607,497 B2 | 8/2003 | McLeod et al. | |
| 7,292,151 B2 | 11/2007 | Ferguson et al. | |
| 7,492,268 B2 | 2/2009 | Ferguson et al. | |

FOREIGN PATENT DOCUMENTS

| | | |
|---|---|---|
| TW | I274862 | 3/2007 |
| TW | M337349 | 8/2008 |
| TW | I307635 | 3/2009 |

\* cited by examiner

*Primary Examiner* — Tai T Nguyen

(74) *Attorney, Agent, or Firm* — Muncy, Geissler, Olds & Lowe, PLLC

(57) ABSTRACT

A human body balance signals measuring system and the method of analysis thereof that has a measuring device, a filter amplifier, an A/D convertor (analog to digital convertor), a signal receiving module, and a data analyze module. The measuring device is linked with the filter amplifier. The filter amplifier can detect and collect the voltage signals caused by pressure change and then filter and amplify the signals. The signals are send to the A/D convertor to convert the analog circuit signals into digital signals for the receiving module to use these voltage change values for human body center of gravity offset evaluation to obtain the COP (center of pressure) offset and COP offset velocity. The data analyze module uses the measured body center of gravity offset for MSE (multiscale entropy) to quantitative the dynamic of human body center of gravity and verify the accuracy of this measuring system.

13 Claims, 26 Drawing Sheets

SYSTEM FOR MEASURING BODY BALANCE SIGNALS AND A METHOD FOR ANALYZING THE SAME

BACKGROUND OF THE INVENTION

1. Field of the Invention

The present invention relates to a system for measuring human body balance signals and a method for analyzing the same, in particular, a system used to evaluate the sense of balance, mainly by measuring the features of balance-related physiological signals from the human body to establish risk assessment indicators for falling down.

2. Brief Description of the Prior Art

According to statistical results, senior citizens have a higher rate of falling down than other age groups. Fall-related injuries are the primary cause of hospitalization and the second highest cause of accidental death for seniors. If an elderly person falls down, body and mental recession become faster because of slower recovery, lack of exercise when in bed and less body movement. Moreover, the elderly usually will also need long-term assists from other family members or caretakers which can cause burdens to the family resulting in emotional and relationship problems.

To prevent elderly people from falling down, the reasons for falling must first be studied. Falling down is a result of loosing body balance. The causes for this are many but in most cases for the elderly; it is because of unintentional loss of balance. As a result, it becomes important to regularly detect the sense of body balancing and make proper adjustments to thereby effectively prevent falling accidents.

All the following articles point out current balance measuring systems which are suitable for lab experiments but not suitable in daily use:

(1) U.S. Pat. No. 5,388,591 (Article 1)

Article 1 mentions maintaining an upright position involves complex senses like vision and hearing which affect the sense of balance. This human posture control system first measures and calculates the COP (center of pressure) movement on feet and time intervals and with changes in vision and hearing to study if the sense of balance is improved. This invention requires complex theories and measures many sensing signals that are usually obtained in a lab. It is difficult for the public to use such a system at home and is not suitable for the general public.

(2) U.S. Pat. No. 5,627,327 (Article 2)

Article 2 mentions standing on an unstable platform for measuring balance. Because of the changes on the platform, the patients' adaptability must rapidly adjust to adapt to the moving platform. The system calculates the samples' sense of balance with monitors and surveillance video systems. This method takes a lot of time and had space limitations. Also, the method requires someone to stand on an unstable platform. This method is not suitable the elderly and certain other members of the public.

(3) U.S. Pat. No. 5,830,158 (Article 3)

Article 3 mentions a system similar to the one in Article 2 but differs in using a sensor under the unstable platform that sends the patient's standing position to a computer for it to display on a monitor in front of the patient. The patient on the test must try to move his COG (center of gravity) to the designated destinations. The sense of balance is analyzed from the data collected. This method also need a lot of time, has space requirement problems, and is not suitable for the elderly.

(4) U.S. Pat. No. 6,063,046 (Article 4)

Article 4 is about a system composed of force sensors, body movement sensors, and EMG (electromyography) electrodes. The force sensors provide the toe-end and heel-end center of pressure change before and after the measurement to the processor. The body movement sensors convert the signals they collected to detail angular position and velocity data for the processor. The EMG electrode signals are amplified to provide muscle movement data to the processor. The processor combines these three data for body balance signals. The drawback is these 3 sensors are expensive and can only be used experimentally but cannot be widely adopted.

(5) U.S. Pat. No. 6,237,256 (Article 5)

Article 5 is about a balance measuring method for standing on a large moveable platform blindfolded. The platform will suddenly move forward, backward, to the right, or to the left. The three force sensors on the large platform and the cameras record data to analyze the subject's sense of balance. Though the large platform has safety handrail installed, this system is still dangerous for the elderly and not suitable for them.

(6) U.S. Pat. No. 6,561,991 (Article 6)

(7) U.S. Pat. No. 6,607,497 (Article 7)

Articles 6 and 7 are similar. They both have a non-rigid supported vibrating platform whose acceleration sensor records the tester's body movement, uses vibration to measure muscle and skeleton, then the vibration and frequency data are changed into vibration spectra for analysis and evaluation. The vibration on this platform may be uncomfortable for the elderly and so the collected data may not be accurate.

(8) U.S. Pat. No. 7,492,268 (Article 8)

(9) U.S. Pat. No. 7,292,151 (Article 9)

Articles 8 and 9 provide an interactive monitoring system with sensors and input control, using wireless communication and monitoring equipments to receive signals and automatically responds with specific answers. This invention is directed to evaluating sports so it is more helpful in observing athletes but not for use by others.

(10) U.S. Pat. No. 5,919,149 (Article 10)

Article 10 is about a system based on balance calculation and how people would react to maintain the stability of a body position and speed when they are not stable. This invention uses light-weight and durable vibration sensors and speed sensors attached to the upper body. Improvement of balance is determined by the angular movements and speeds signals from the sensors. This method needs to attach sensors on the body during the test and they are not easily carried. Multiscale entropy (MSE) could instead be more accurate than simply using angular speed for analysis.

(11) Republic of China (Taiwan) Patent 200821015 (Article 11)

Article 11 is a dynamic posture balance training system composed of foundation and tilting platform controlled by power and vibrating mechanism to move and vibrate the training platform. A sensor is configured to sense the down pressing weight of the user, and a receiving module is configured to receive the signals from the sensor for analyzing the different center of pressure under different motions like moving, vibrating, and turning. This patent needs a person standing on a moveable platform and then calculates the data with the platform moving. Accordingly, the system is not suitable for the elderly.

(12) Republic of China (Taiwan) Patent 094130876 (Article 12)

Article 12 has equipment to cause voltage change but does not further analyze the produced signals for human body center of weight offset. As will be explained, the present invention is better for it measures and collects the platform data, uses program written in MatLab to transfer the data into a diagram for a human body movement offset, then use MSE (multiscale entropy) to analyze the data, and numerically present the balance conditions of the tester.

(13) Republic of China (Taiwan) Patent 096217876 (Article 13)

Article 13 uses a three-axis accelerometer to measure voltage change which is different from our way of using load cell. Our amplifying circuit board also has the filtering function to reduce noise. The analysis method is different too as will be explained. Article 13 uses acceleration as the quadratic differential of displacement to determine body movement which is not very accurate. The present invention directly analyzes the offset of center of weight which is a better solution.

According to the above mentioned thirteen (13) articles, current systems that measure the sense of balance are used in the lab for experiments and they are expensive and complicated to operate. The manufactures would not mass produce this precision equipment and it could not be easily afforded and accessible for the public. Because it takes a lot of time for treating the balancing problem, patients must often go to major hospitals or medical centers for detecting the sense of balance. This can become a transportation and cost burden for patients so that treatment could not be maintained thereby resulting in the interrupt of the treatment.

The known current practice has a lot of drawbacks, is not a good design, and must be improved.

SUMMARY OF THE INVENTION

The primary objective of this invention is to provide a body balance measuring system and analysis method which offers a system to evaluate the sense of balance, offers earlier discover of problems and offers a resolution to the problem of falling down.

Another objective of this invention is to provide a body balance signals measuring system and analysis method which can be available for the public at a reasonable cost.

The body balance measuring system and analysis method of the present invention meets the mentioned objectives. This system has a measuring system a measuring device, with a filter amplifier, an A/D converter (analog to digital converter), a signal receiving module, and a data analysis module. The measuring device is linked with the filter amplifier so the voltage signals collected by the measuring device caused by pressure change is amplified by the filter amplifier. The A/D convertor then converts the analog circuit signals into digital data for the receiving module. As a result, the voltage change data is then used in the body center of weight offset analysis to obtain the COP (center of pressure) position offsets and COP offset velocities. The data analysis module uses the MSE data from the offsets of center of weight movement to analyze for the dynamic characteristics of human body center of weight offsets and verify the accuracy of this system.

This invention uses MSE theory to analyze the complexity of human body center of weight balancing. The results indicate MSE is a proper way to analyze the signals related to center of weight and the outcome of MSE evaluation and analysis is very accurate.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENT

Figure 1:
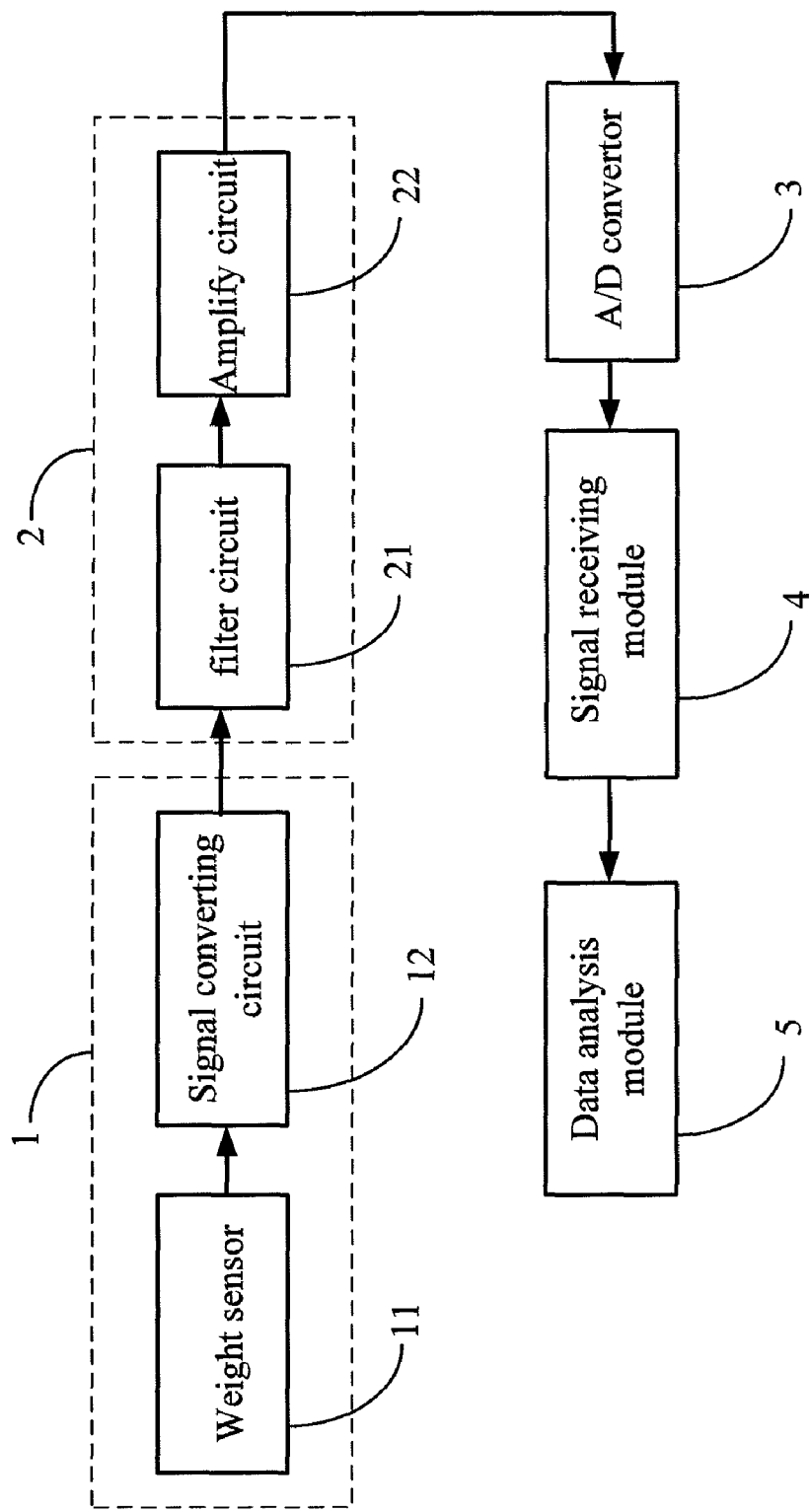
FIG. 1 shows the system layout of the body balance measuring system and analysis method of the present invention.

Referring to FIG. 1, the system layout of the body balance signals measuring system of the present is shown. This system includes a measure device 1 that is linked to a filter amplifier 2 where the measure device 1 can capture the voltage signal for pressure change and send this signal to the filter amplifier 2 for processing. The measure device 1 in this invention uses electronic weight scales that are easily obtained on the market for their weight sensor 11. It is contemplated that this invention uses four weight sensors. The weight sensor 11 is connected to a signal converting circuit 12. The weight sensor 11 and signal converting circuit 12 form the measure device 1. An electronic weight scale has the same pressure sensing method as a strain gauge. The sensor within is deformed to cause a change in resistance under pressure so if the input voltage is constant, resistance is changed according to the force. By measuring the voltage change, the signal converting circuit 12 can obtain the voltage signals caused by pressure changes. The signal converting circuit 12 uses a Wheatstone bridge circuit to collect the voltage signals and should be able to measure the slightest resistance difference in order to have precise information. The characteristic of the Wheatstone bridge circuit is that it can measure this tiny resistance change. In the strain gauge situation, the Wheatstone bridge circuit has three types as four active gauges (full bridge), two gauges (half bridge), and a single gauge (quarter bridge). These three types of circuits are different in output conditions and noise interferences to be the most suitable type is chosen according to the situations.

The filter amplifier 2 is interfaced between the measure device 1 and an A/D convertor 3. This filter amplifier 2 includes a filter circuit 21 and an amplify circuit 22 to filter and amplify the signals collected by the measure device 1 and to send the signals to the A/D convertor 3. This filter circuit 21 can be either analog or digital and this invention uses the simple resistor capacitor filter circuit for signal filtering. The amplify circuit 22 mainly amplifies the bridge circuit output voltage and this invention uses INA118 amplifying chip to amplify the signals.

The A/D convertor 3 interfaces with the filter amplifier 2 and a signal receiving module 4 to convert the analog voltage signals processed by filter amplifier 2 into digital signals and then sends the signal to the signal receiving module 4.

The signal receiving module 4 is connected to the A/D convertor 3 and a data analysis module 5. The signal receiving module 4 also stores the digital signal outputs from the A/D convertor 3. The signal receiving module 4 used in this invention is a signal receiving interface programmed with Boarder C++ Builder (a programming language) that can store the received signals as .txt files for analysis.

The data analysis module 5 is connected to the signal receiving module 4 to analyze the voltage variations (voltage signals) it receives from the A/D convertor 3 for human body center of weight offsets, COP position offsets, and COP offset velocities. The COP position offsets and COP offset velocities are further analyzed to obtain MSE curve, MSE curve complexity and its one-way variance. The data analysis module 5 uses the measured body center of weight offset multiscale entropy to quantify the dynamic characteristics of body center of weight offsets and to verify the accuracy of this measurement. This data analysis module 5 uses MATLAB as a primary signal value analysis system. Since the signals converted by the A/D converting board still has notable noises, a numeric method can be used to eliminate the noise before analyzing then use MSE and other non-linier analysis method to analyze the processed data. Also, the A/D convertor 3 in this invention can be replaced with an embedded system. For example, an advanced RISC machine (ARM system), can be used where the embedded system can catch the digital signals from the measure device 1. An ARM system can also reduce the cost of the entire measuring system, convert the signals, analyze the data, and display the results.

Figure 2:
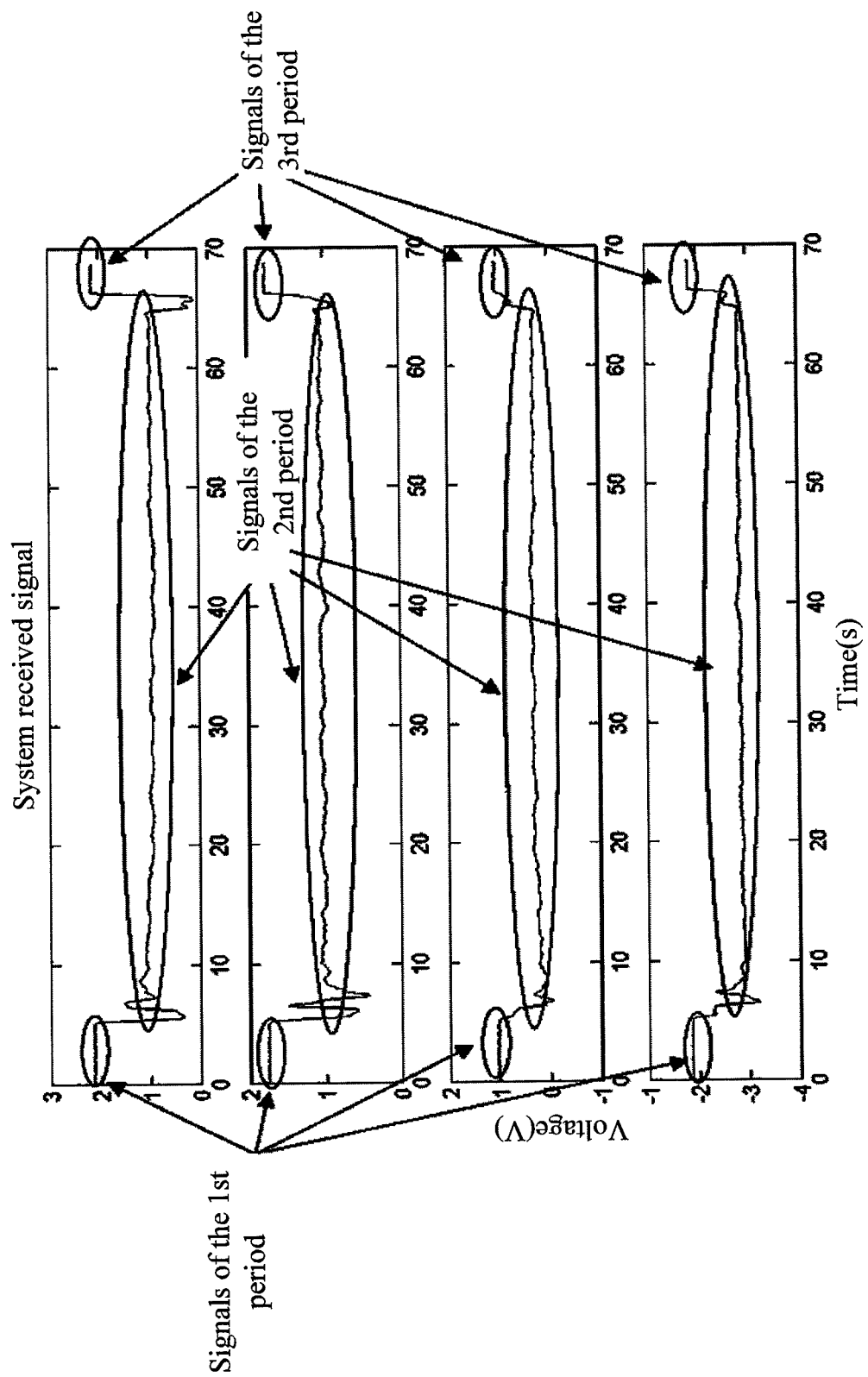
FIG. 2 shows the COP voltage signals measured in the present invention.

Turning now to FIG. 2, the COP measured voltage diagram of this invention is shown. The measuring collects three periods of signals from four measuring devices which are marked separately. FIG. 2 shows there when there is no loading at the first period, the result is a straight line. The voltages at the four measuring devices are 1.95 volts, 1.6 volts, 1.3 volts, and −0.05 volts. At the second period, body weight caused the voltage changes and the voltage ranges for the four measuring devices are 0.7~1.1 volts, 1~1.3 volts, 0.8~1.2 volts, and −1.2~0.8 volt. At the beginning and the end of the second period the test subject entered and left the system platform causing the waves in the records. In the third period, the voltage signals return to the base voltages as there is no loaded weight since the subject left the platform.

Figure 3:
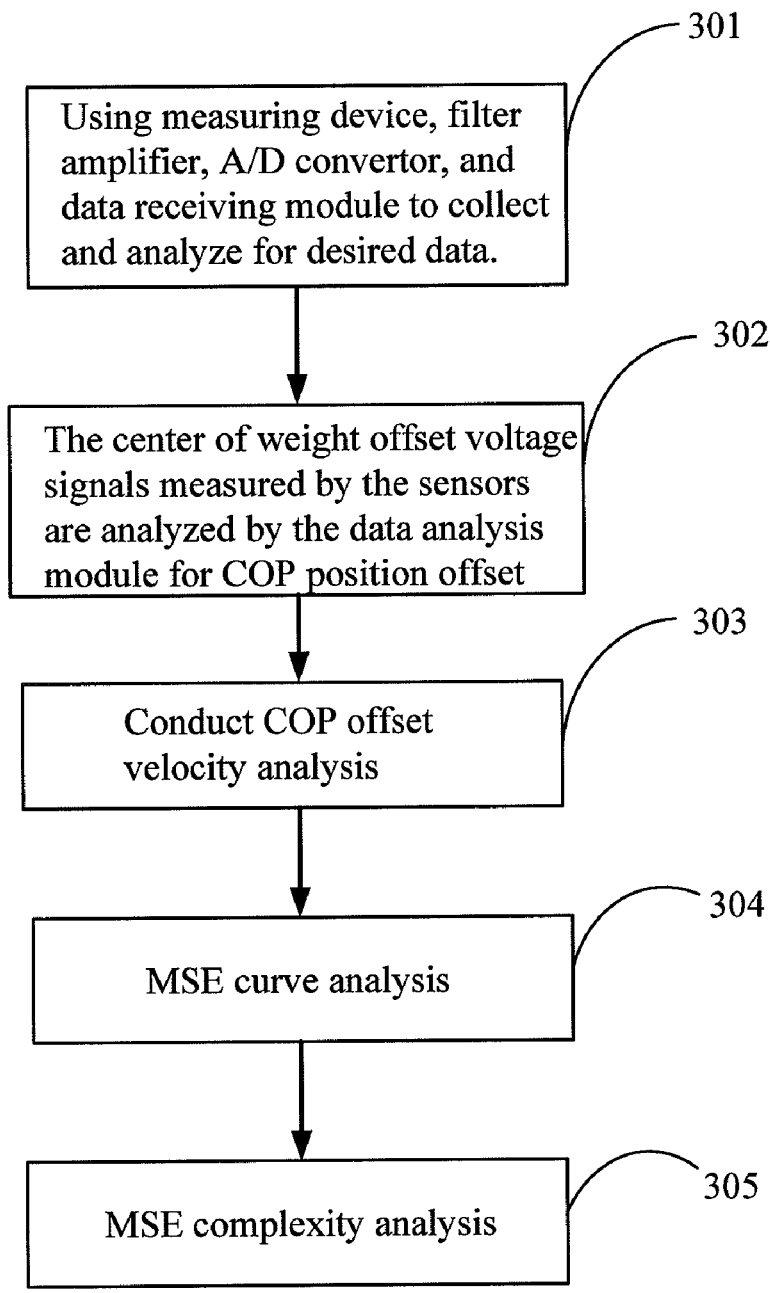
FIG. 3 shows the signal analysis flowchart of the present invention.
Figure 4:
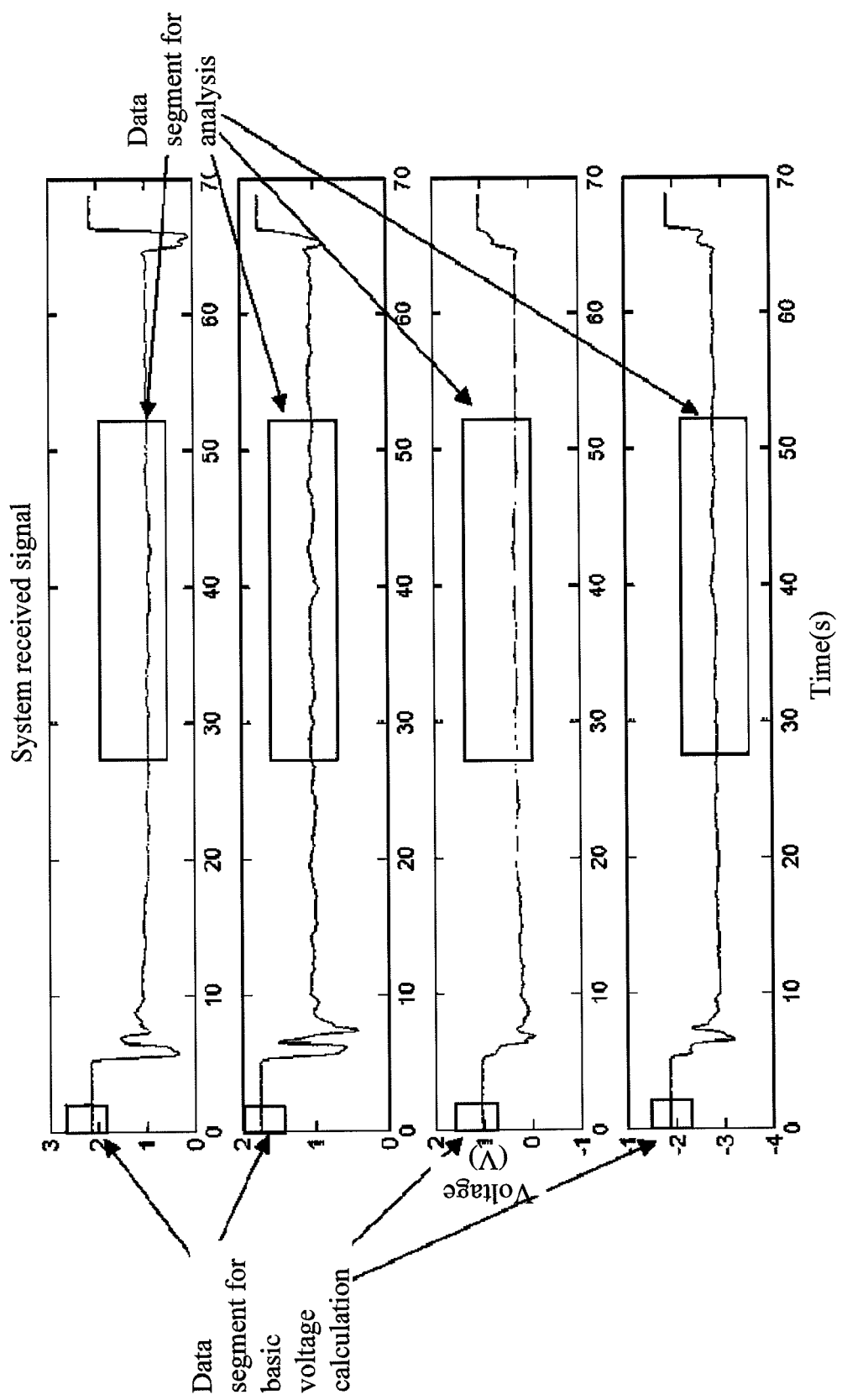
FIG. 4 shows the signal analysis illustrating diagram of the present invention.

In FIG. 3, the signal analysis flowchart of this invention of body balance signals measuring system and the analysis method where the body balance signal analysis method is shown. This signal analysis flowchart has the following steps:

1. The desired data 301 for analyzing are retrieved by the measuring device, filter amplifier, A/D convertor, and data receiving module. As shown in FIG. 4, the average of the voltage data of the first two seconds in the first period is retrieved and denoted as the basic voltage. The body weight loaded voltage data during the twenty-eight seconds of the second period are then retrieved. Then subtracting the basic voltage of each sensor from the body weight loaded voltage sensed by the four sensors subtract to result in the center-of-weight offset voltage signals.

Figure 5:
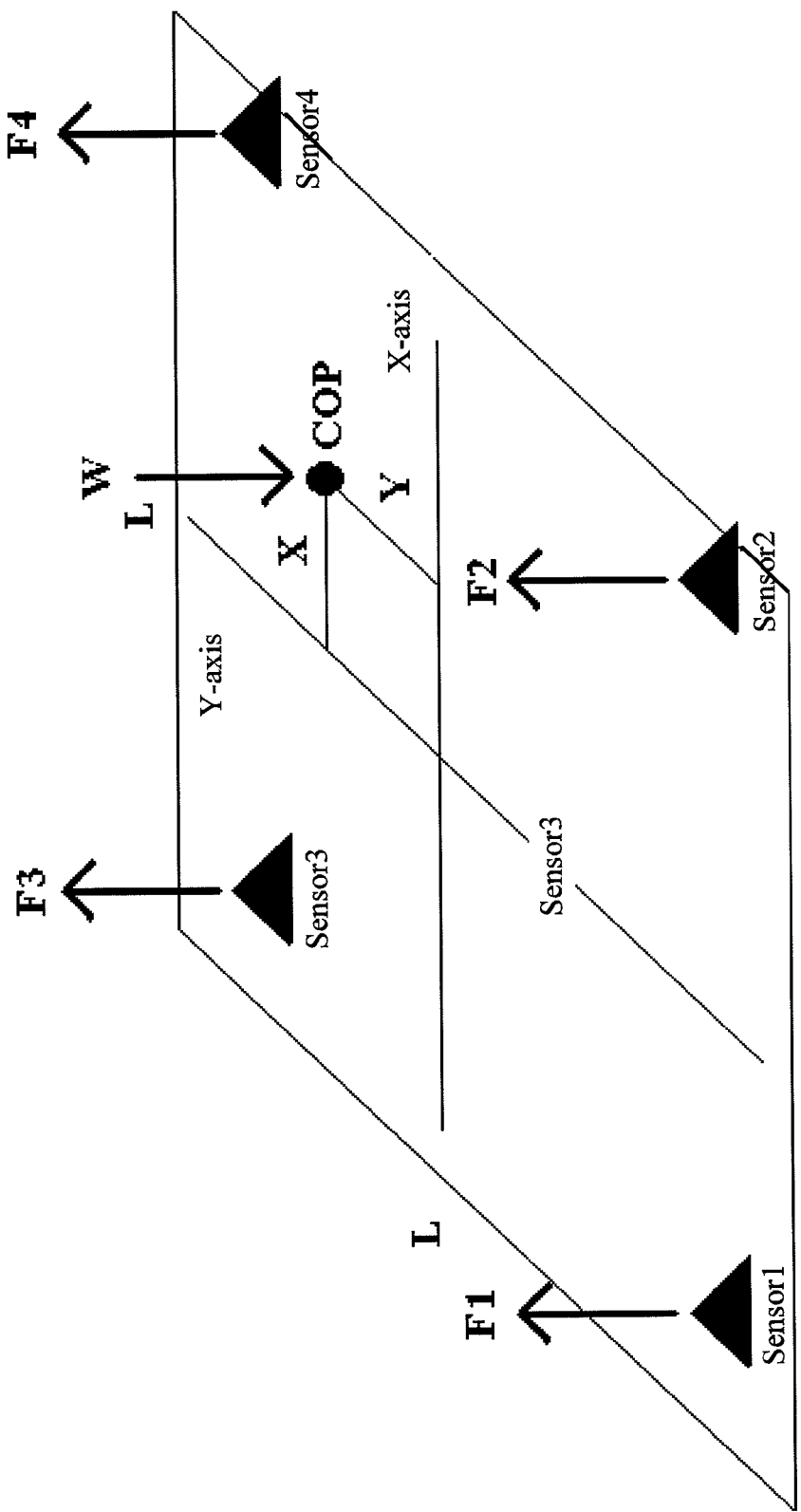
FIG. 5 shows the COP analysis illustrating diagram of the present invention.

2. The center-of-weight offset voltage signals measured by the sensors are analyzed by the data analysis module for COP position offset 302 mainly by analyzing COP for COP position and the COP analysis method is shown in FIG. 5. When the loaded weight (W) is applied to the four sensors, counter forces F1, F2, F3, and F4 are generated. The distance between the sensors is L, and the X-axis and Y-axis coordinates for the COP can be set as X-axis (the left-and-right direction) and the Y-axis (the back-and-forth direction). Hence, the COP components on the X-axis and Y-axis are calculated respectively as:

$$X = \frac{[(F4 + F2) - (F1 + F3)] \times L}{W}$$
$$Y = \frac{[(F3 + F4) - (F1 + F2)] \times L}{W}$$

where loaded weight W=F1+F2+F3+F4, and COP=(X,Y);

3. COP offset velocity analysis 303 is then undertaken. COP offset velocity is calculated by using the COP position minus the last sampled COP value and divided by sampling time. COP offset velocity also has the left-and-right and back-and-forth directions;

4. The MSE curve 304 is then analyzed. In SampEn (Sample Entropy, a statistic analysis method by Joshua S. Richman and J. Randall Moorman) MSE analysis, the N value for the largest SCALE is best to be between 300 and 500 so the MSE analysis parameter N is set as 350 and the largest SCALE is set as 10. The 14,000 recorded data with sampling frequency of 500 Hz are transferred into 3,500 recorded data with sampling frequency of 125 Hz to make the N value to 350 with the largest SCALE as 10;

5. The $C_I$ value (complexity indexes) is analyzed. $C_I$ is defined as the area beneath the MSE curve used to analyze the MSE complexity 305. The equation is:

$$C_I = \sum_{i=1}^{10} SampEn(i)$$

Where $C_I$ represents the complexity and i represents the number of scales.

This invention uses some tests to verify the system and has the following examples:

By measuring system noise and/or signals when standing on the right foot and both feet, it is able to test if the measuring system can tell the difference of COP status (system noise, balance signals for standing on one foot, and balance signals for standing on both feet). Because the one-foot balance signals and the two-foot balance signals of the same person are different and the measured balance signal data should be different, the non-linier theory analysis results are different too. So by telling the difference in the analysis for one-foot and two-foot measured data, this invention is proved to recognize the difference for different balance signals.

In measuring the elderly and the youth for their body balance signal data to analyze for the balance signal differences between these two groups, it is needed to establish the balance index to warn those with higher risk of falling down and to prevent it from happening.

Figure 6:
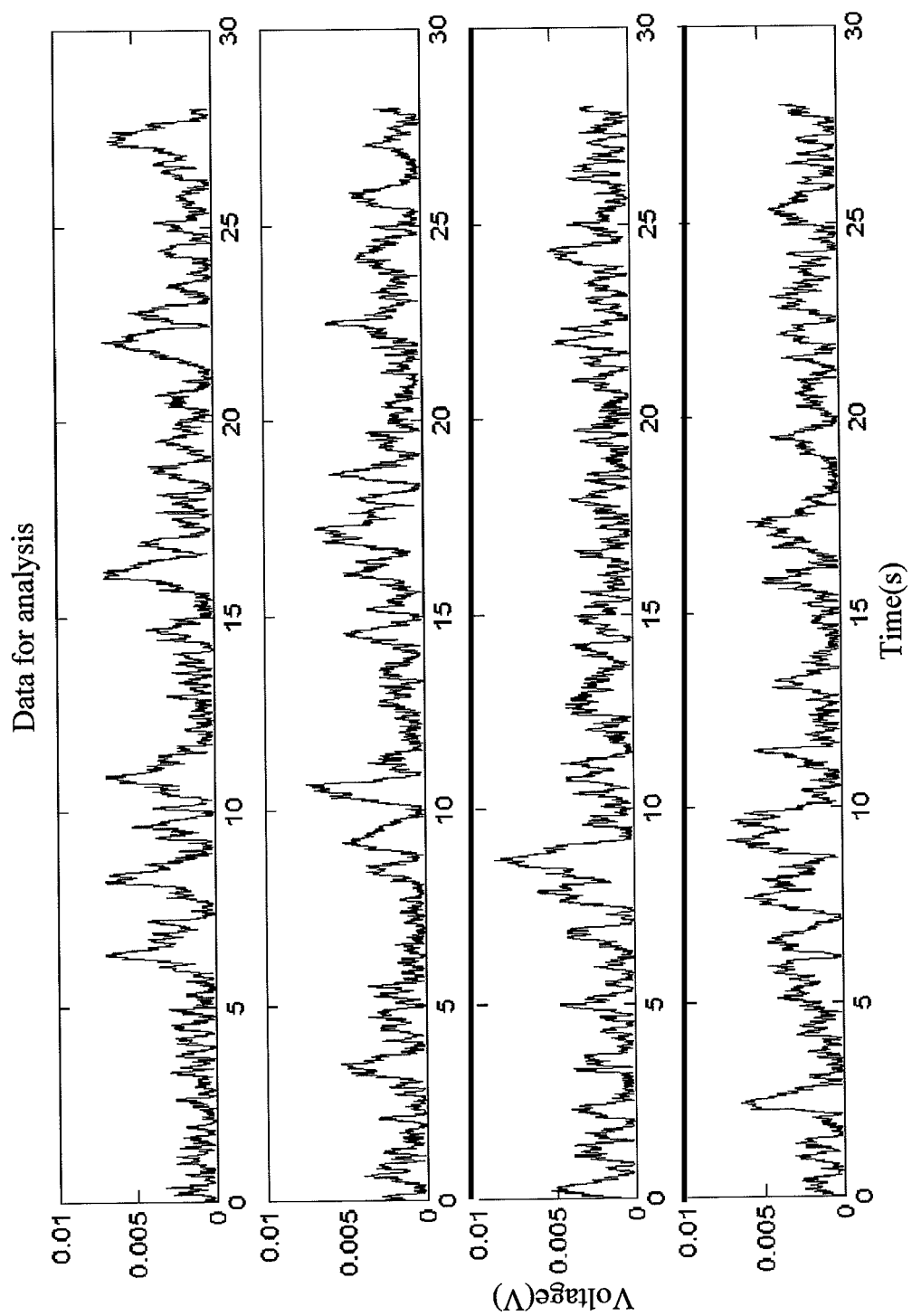
FIG. 6 shows the voltage signal diagram without loaded weight of the present invention.

Please refer to FIG. 6 for the voltage signal diagram without loaded weight of this invention of body balance signals measuring system and the analysis methods. For the system noise COP status, since there is no loaded weight, the COP position status is interfered by the system noise. The signals are measured without loaded weight for a sampling time of 70 seconds with sampling frequency of 500 Hz.

Figure 7:
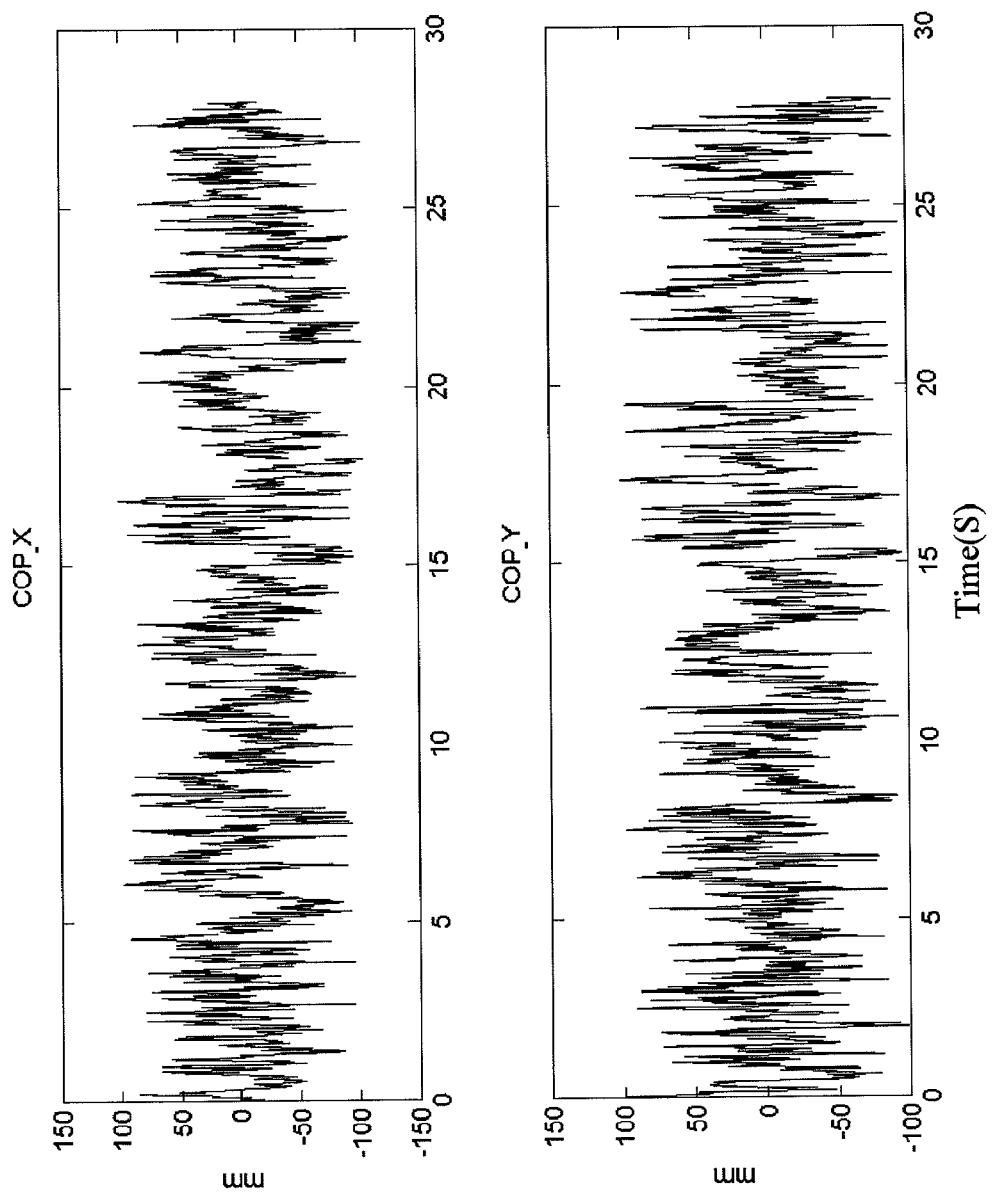
FIG. 7 shows the COP_X and COP_Y analysis diagram without loaded weight of the present invention.
Figure 8:
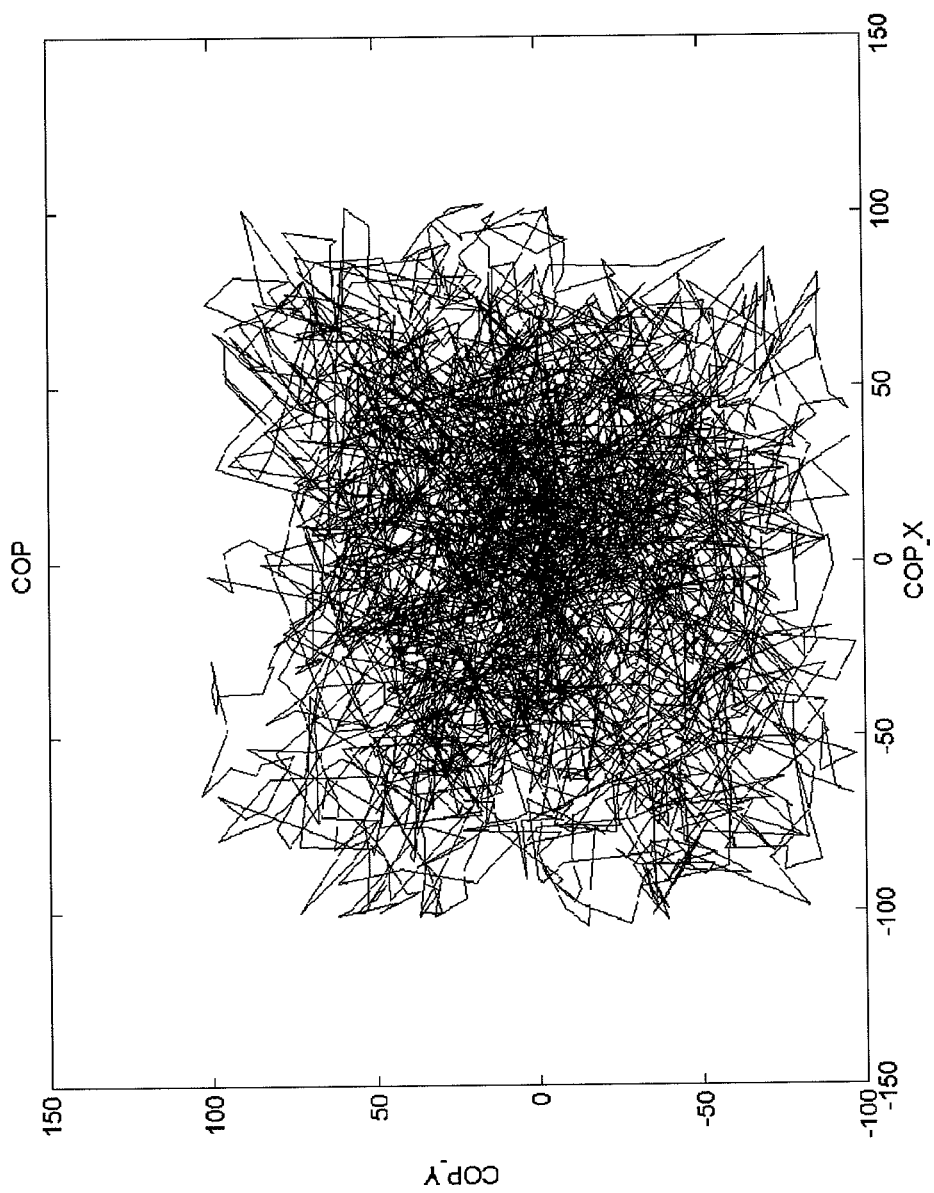
FIG. 8 shows the COP position offset without loaded weight of the present invention.

In the system noise test, as seen in FIG. 6, the captured data was the system noise signals and the measured voltage signals for the four sensors are between 0 and 0.008 volt. After COP analysis, the system noise COP variation is shown in FIGS. 7 and 8. In FIG. 7, COP_X represents the COP position variation in the left-and-right direction, COP_Y represents the COP position variation in the back-and-forth direction. It is clearly seen that the COP has a lot of turbulence in both directions. FIG. 8 shows the COP position offsets in both directions and the COP variation is turbulent. The signals caused by the system noise were too messy to tell the changes in COP offset because the COP analysis is a proportion analysis method. Though the voltage variations on the four sensors are small, the denominator in COP analysis is also small so the analysis results varies a lot and have the messy COP offset result.

Figure 9:
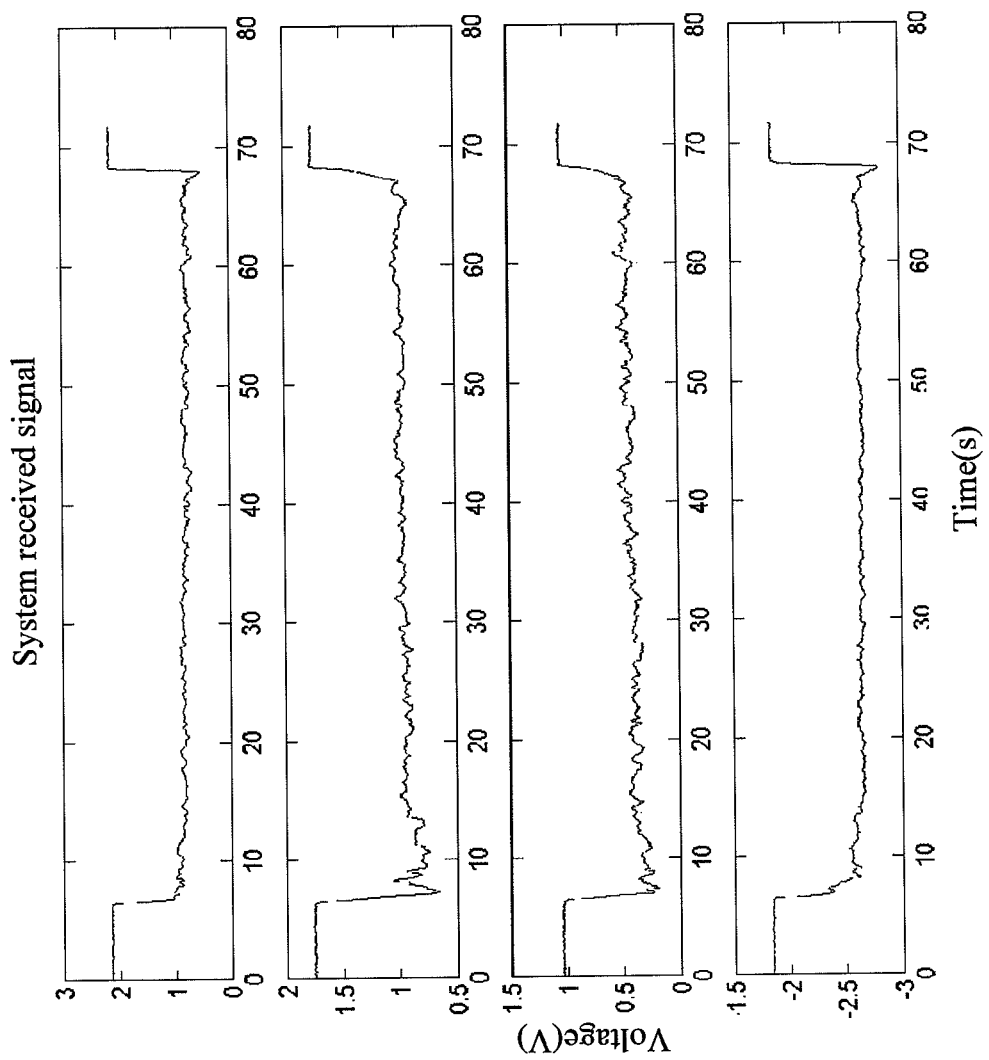
FIG. 9 shows the received voltage signal diagram when standing on one foot of the present invention.

Referring to FIG. 9, the voltage signal diagram measured when standing on one foot for this invention is shown. During the test of standing on one foot, all test subjects are required to stand on the right foot. Before going to the platform, the voltage signal was recorded for five seconds for the initial voltage signal and while standing on the platform, signal was collected for 60 seconds at the frequency of 500 Hz.

Figure 10:
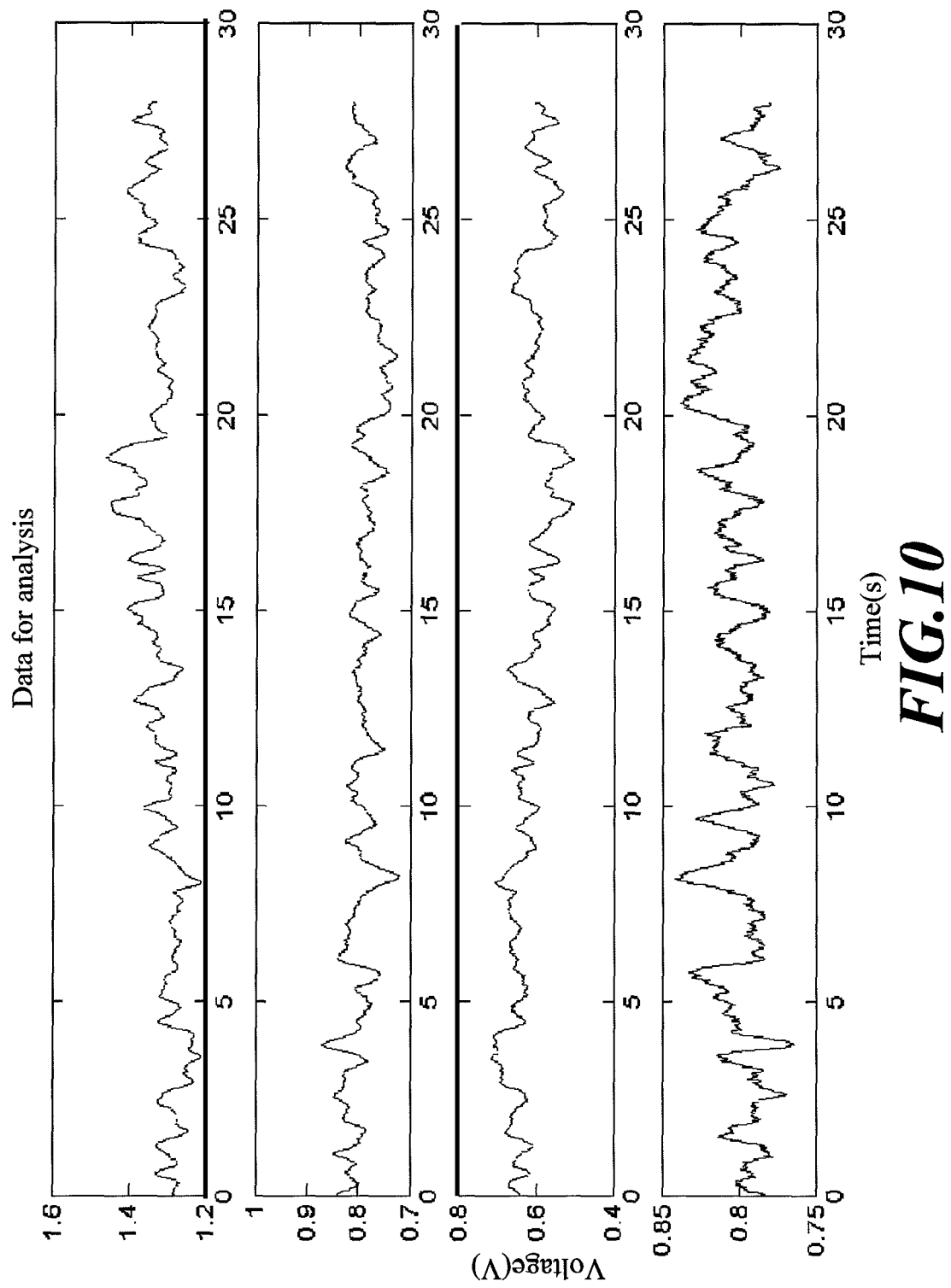
FIG. 10 shows the retrieved voltage signal diagram when standing on one foot of the present invention.
Figure 11:
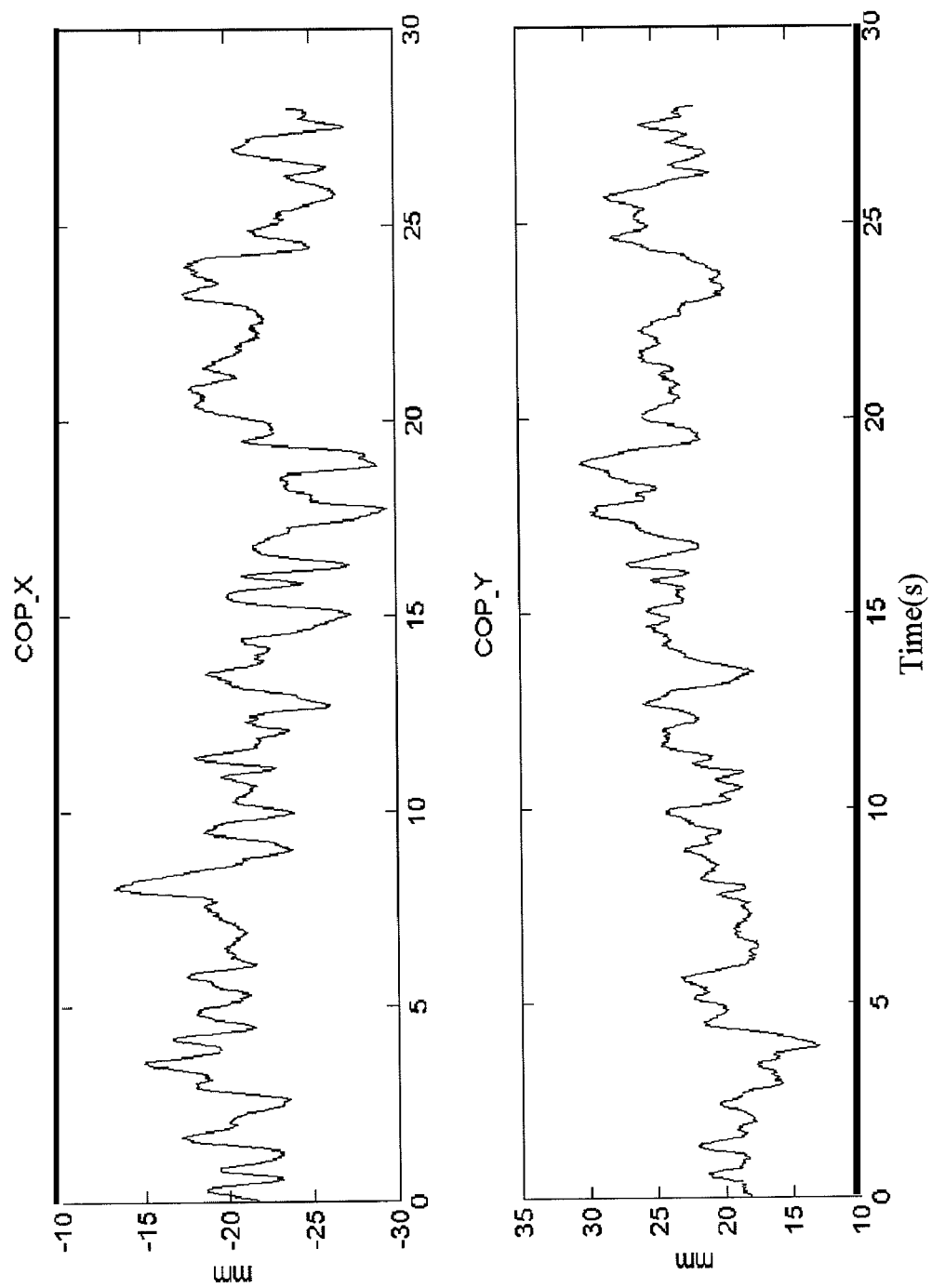
FIG. 11 shows the COP_X and COP_Y analysis diagram when standing on one foot of the present invention.
Figure 12A:
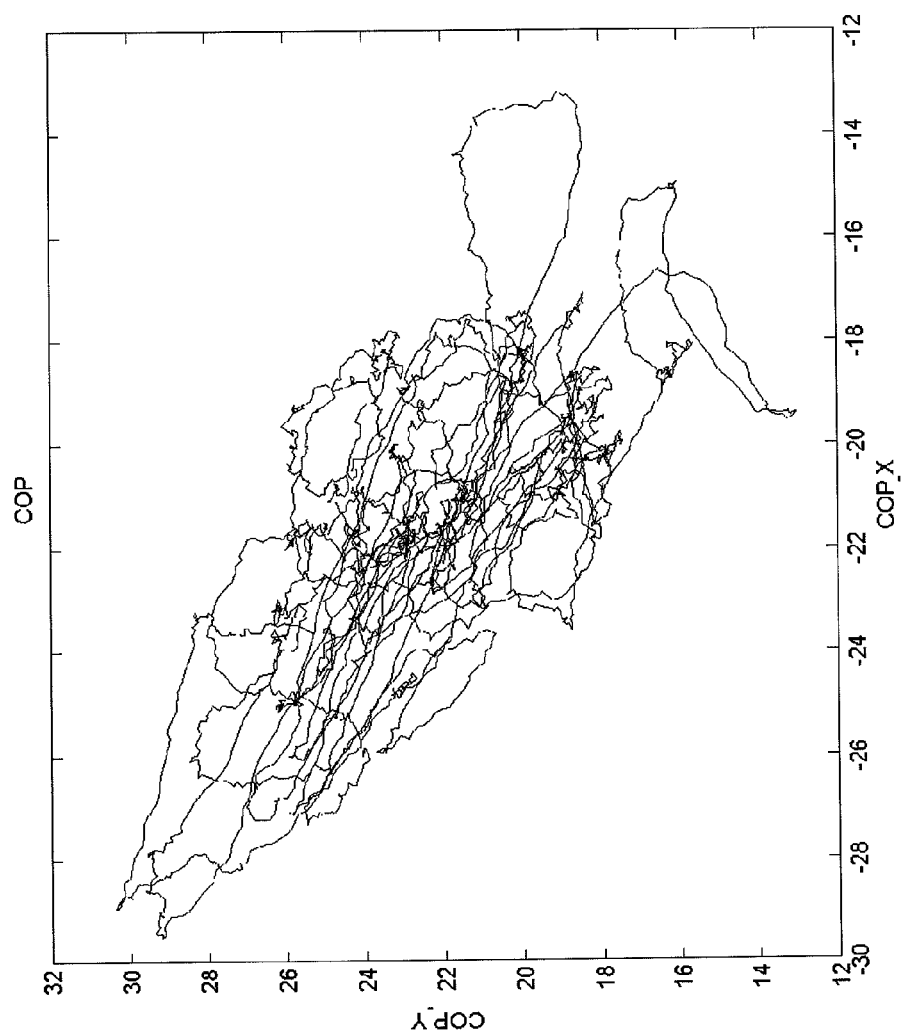
FIG. 12A shows the COP position offset variation when standing on one foot of the present invention.
Figure 12B:
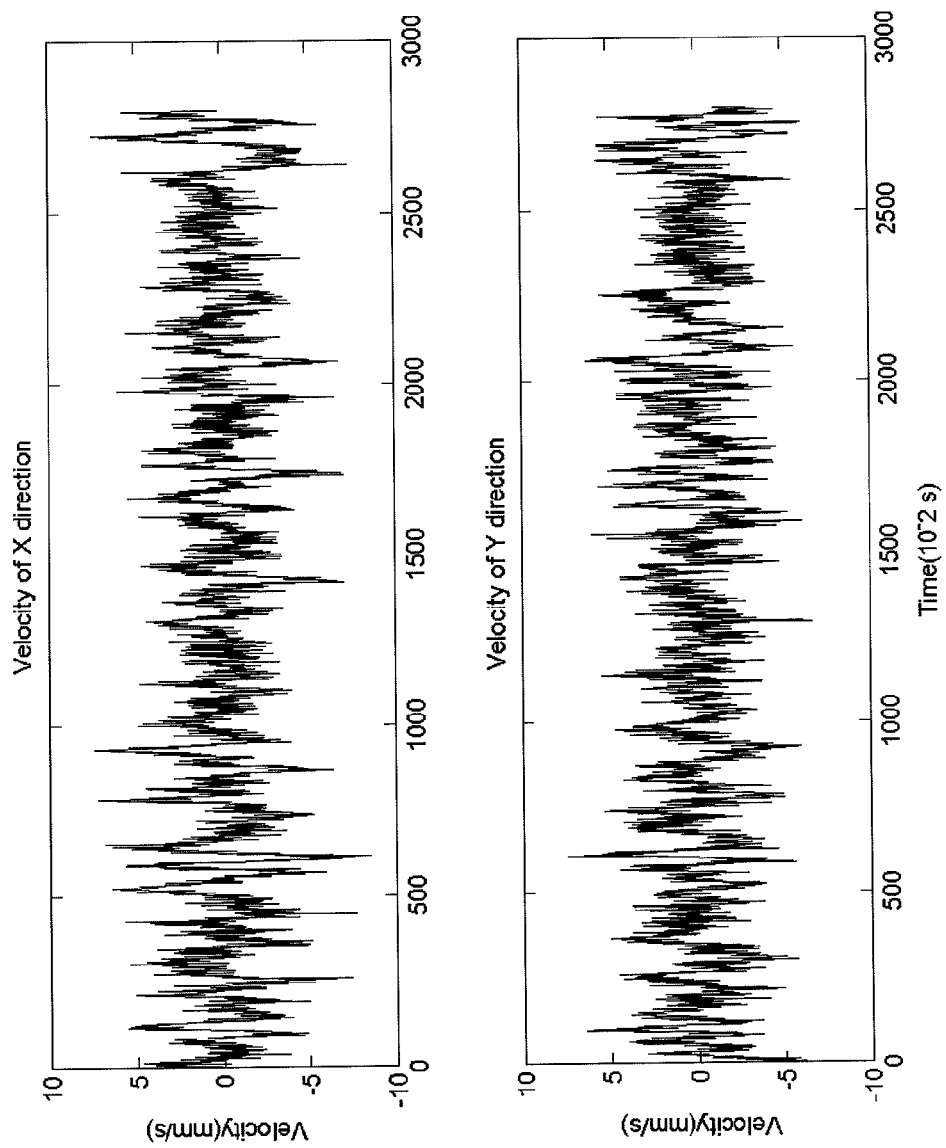
FIG. 12B shows the COP offset velocity variation when standing on one foot of the present invention.

In the test of standing on one foot, the received signal data is shown in FIG. 9 and the segment in analysis is shown in FIG. 10. The voltage variation is greater than the system noise and is around 0.2 volt. After the COP analysis on the data, the COP variation curves for standing on one foot are shown in FIG. 11, FIGS. 12A, and 12B. In FIG. 11, COP_X stands for the COP position variation in the left-and-right direction and COP_Y is the COP variation in the back-and-forth direction. The COP variation in both directions is not as complex as the noise and can tell the changing trend for the COP position in both directions. FIG. 12A shows the COP position offset by combining the variation from both directions and the variation of the COP position offset can be seen. FIG. 12B shows the COP offset velocity variation obtained from the COP position offset.

Figure 13:
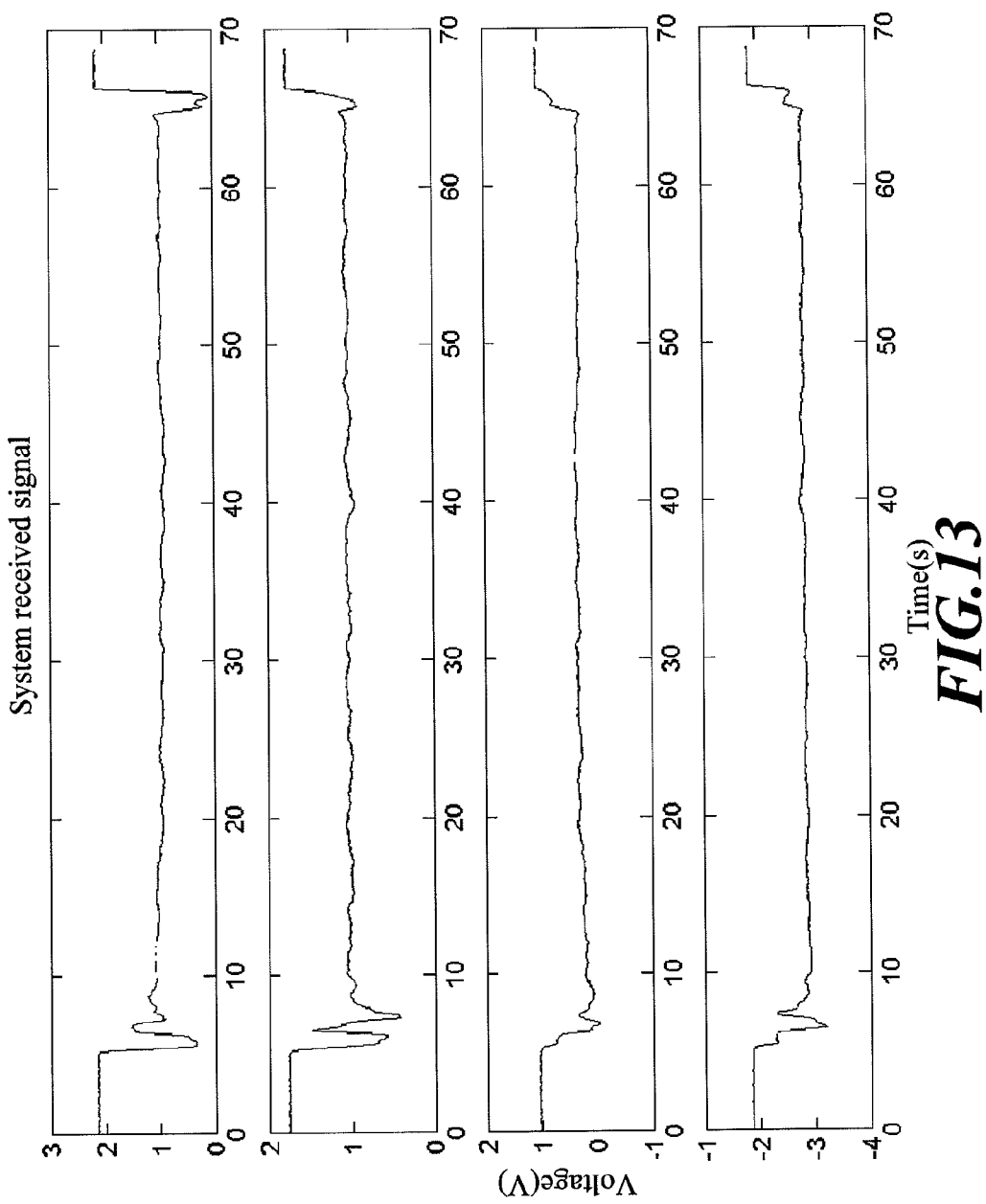
FIG. 13 shows the received voltage signal diagram when standing on two feet of the present invention.

In FIG. 13, the retrieved voltage signal diagram is shown when standing on two feet for this invention. During the test of standing on both feet, voltage signals were recorded for five seconds without loaded weight as the initial point of signal voltage. When the test subject stands on the platform, a measured time of 60 seconds is counted with the same sampling frequency of 500 Hz as in the previous mentioned test. The system noise and the parameters for standing on the right foot and both feet are set up as the following Table 1:

TABLE 1

The system noise and the parameters for standing on the right foot and both feet

| | Measurement | | |
|---|---|---|---|
| items Measuring steps | System noise | One (right) foot balance signal | Two feet balance signal |
| Platform noise period (s) | 70 | 5 | 5 |
| Balance measuring period (s) | N/A | 60 | 60 |
| Sampling frequency (Hz) | 500 | 500 | 500 |

(Note:
N/A means not available)

Figure 14:
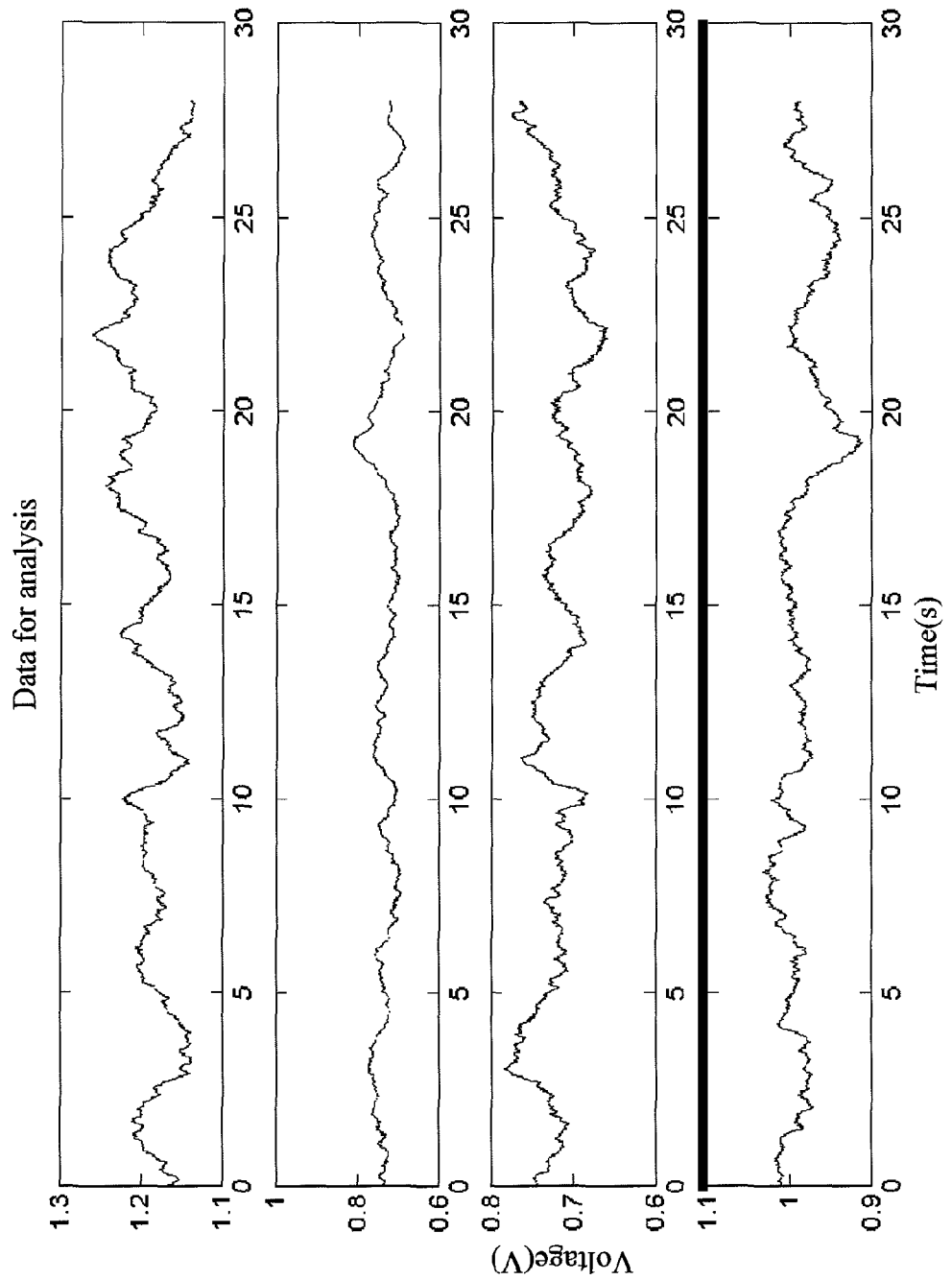
FIG. 14 shows the retrieved voltage signal diagram when standing on two feet of the present invention.
Figure 15:
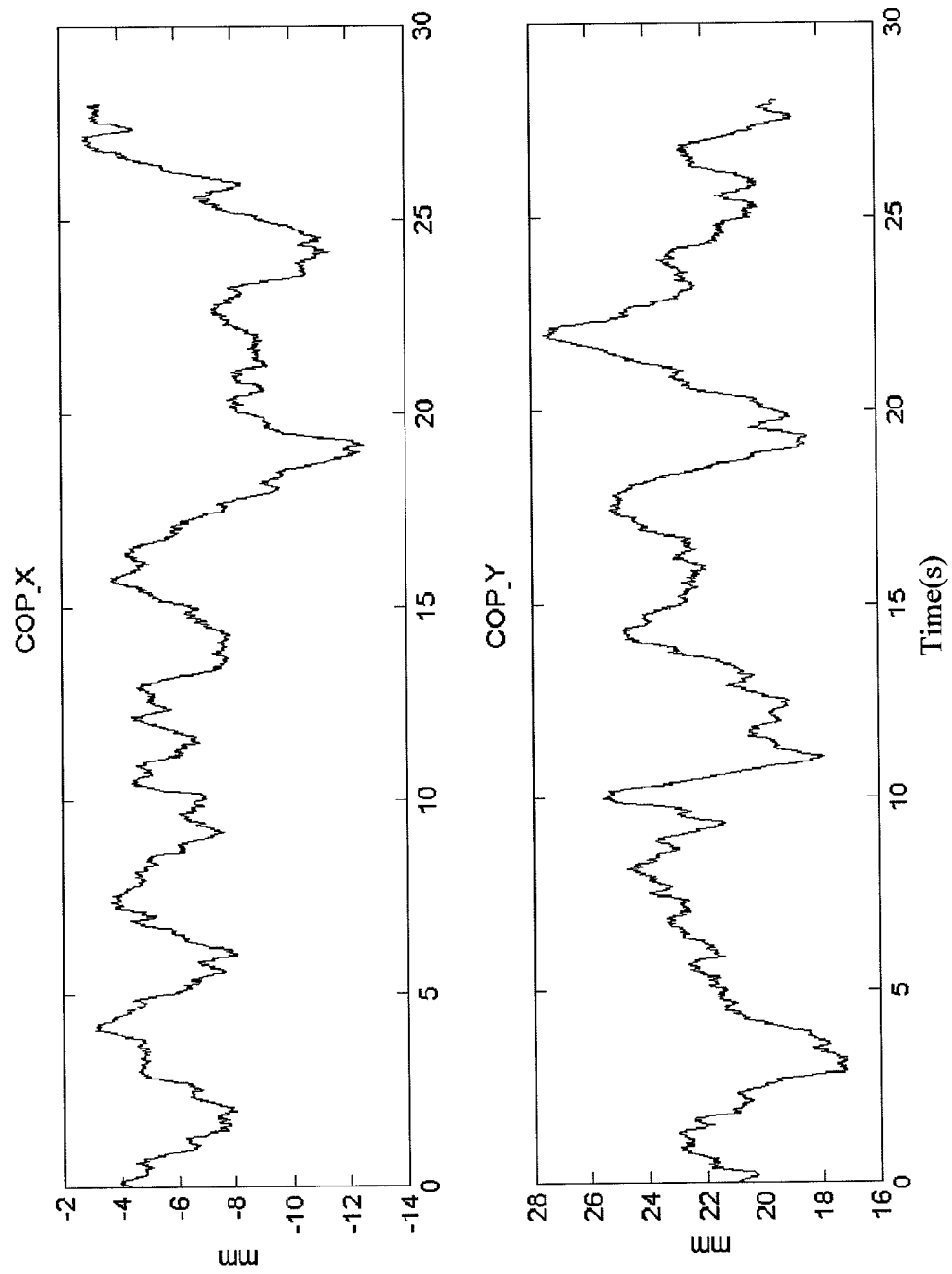
FIG. 15 shows the COP_X and COP_Y analysis diagram when standing on two feet of the present invention.
Figure 16A:
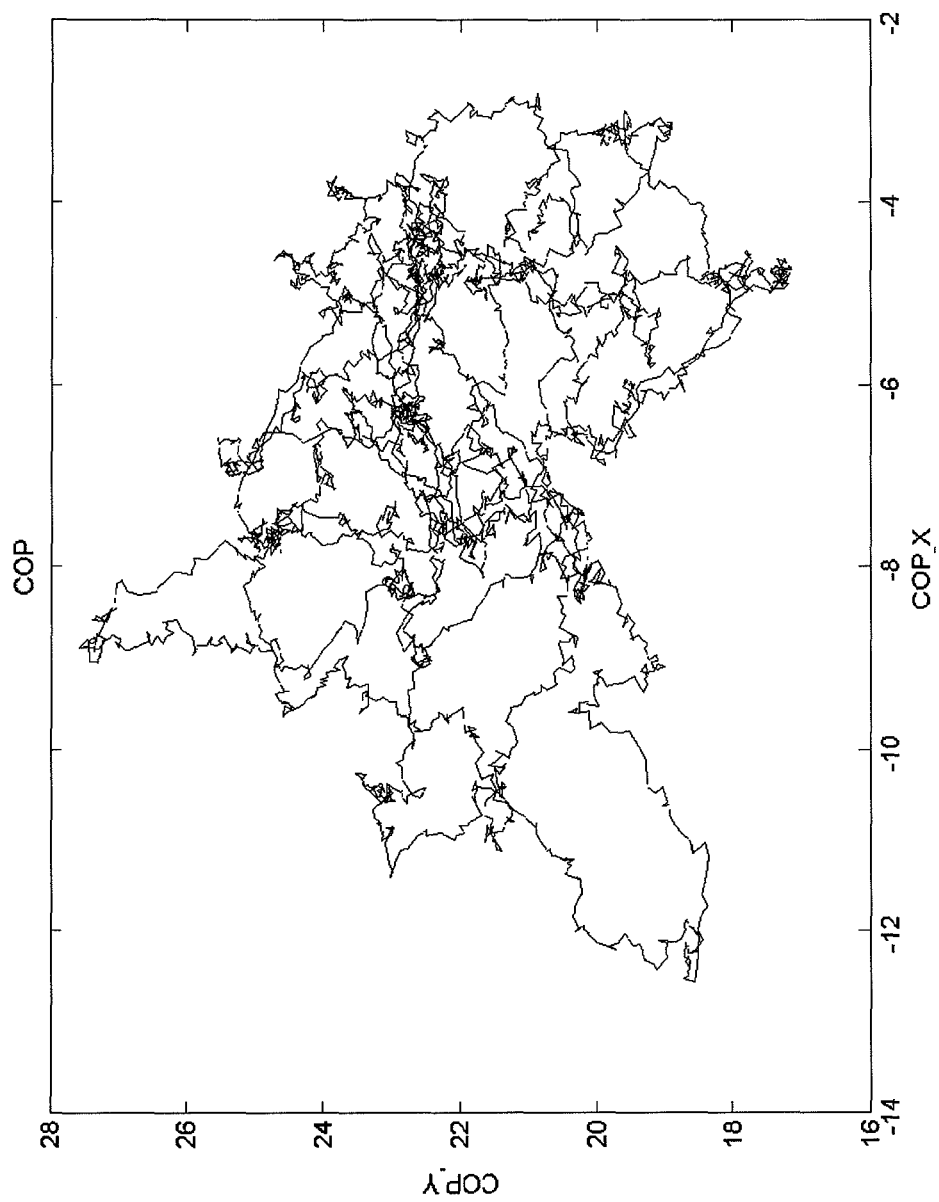
FIG. 16A shows the COP position offset variation when standing on two feet of the present invention.
Figure 16B:
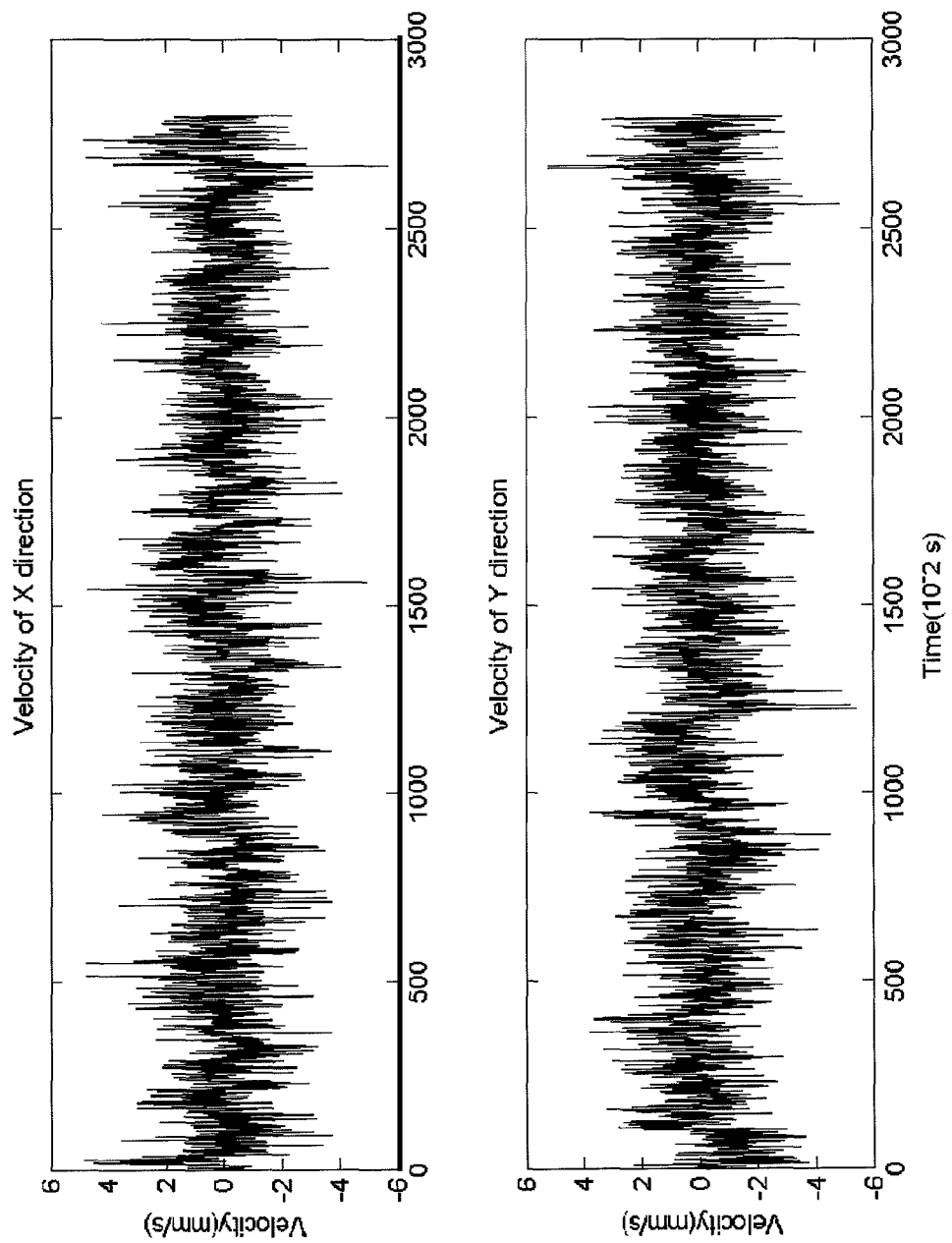
FIG. 16B shows the COP offset velocity variation when standing on two feet of the present invention.

In the test of standing on both feet, the received signals are shown in FIG. 13. It is very different from the system noise result and the variation is smoother compared to the result of standing on just one foot. The segment in analysis is shown in FIG. 14. The voltage variation is within 0.18 volt. After the COP analysis on the data, the COP variation curves for standing on two feet are shown in FIG. 15, FIG. 16A, and FIG. 16B. In FIG. 15, COP_X stands for the COP position variation in the left-and-right direction and COP_Y is the COP variation in the back-and-forth direction. FIG. 16A shows the COP position offset by combining the variation from both directions and the variation of the COP position offset can be seen. FIG. 16B shows the COP offset velocity variation obtained from the COP position offset.

After having COP_X and COP_Y data, the MSE analysis for the one foot and two feet data is conducted. The three parameters in the MSE are the length of time series N=3500, the pattern length m=2, and the similarity criterion r=0.2·SD. The MSE scale is 1 to 10.

The analysis for $C_I$ is performed after having MSE data. Table 2 is the $C_I$ analysis result for COP position and COP offset velocity while standing on one foot and two feet present in the format of average±standard variation, and the P value from t-test statistic analysis is used to represent its variety.

TABLE 2

$C_I$ value analysis for one-foot and two-feet

| $C_I$ (mean ± SD) | COP position | | COP offset velocity | |
|---|---|---|---|---|
| | Left-and-right direction | Back-and-forth direction | Left-and-right direction | Back-and-forth direction |
| One-foot | 4.26 ± 0.78 | 4.07 ± 1.02 | 17.19 ± 0.97 | 17.91 ± 0.88 |
| Two-feet | 3.25 ± 0.25 | 2.89 ± 0.33 | 21.06 ± 0.31 | 20.68 ± 0.23 |
| | | P value | | |
| One-foot vs. Two-feet | 0.024 | 0.041 | $2.761 \times 10^{-5}$ | $1.425 \times 10^{-4}$ |

TABLE 3

$C_I$ value analysis for the elderly and the youth

| $C_I$ (mean ± SD) | COP position | | COP offset velocity | |
|---|---|---|---|---|
| | Left-and-right direction | Back-and-forth direction | Left-and-right direction | Back-and-forth direction |
| Elderly | 2.48 ± 0.76 | 2.30 ± 0.24 | 15.77 ± 2.81 | 16.05 ±± 1.76 |
| Youth | 3.25 ± 0.25 | 2.89 ± 0.33 | 21.06 ± 0.31 | 20.68 ± 0.23 |
| | | P value | | |
| Elderly vs. Youth | 0.068 | 0.018 | $3.773 \times 10^{-3}$ | $5.888 \times 10^{-4}$ |

Figure 17A:
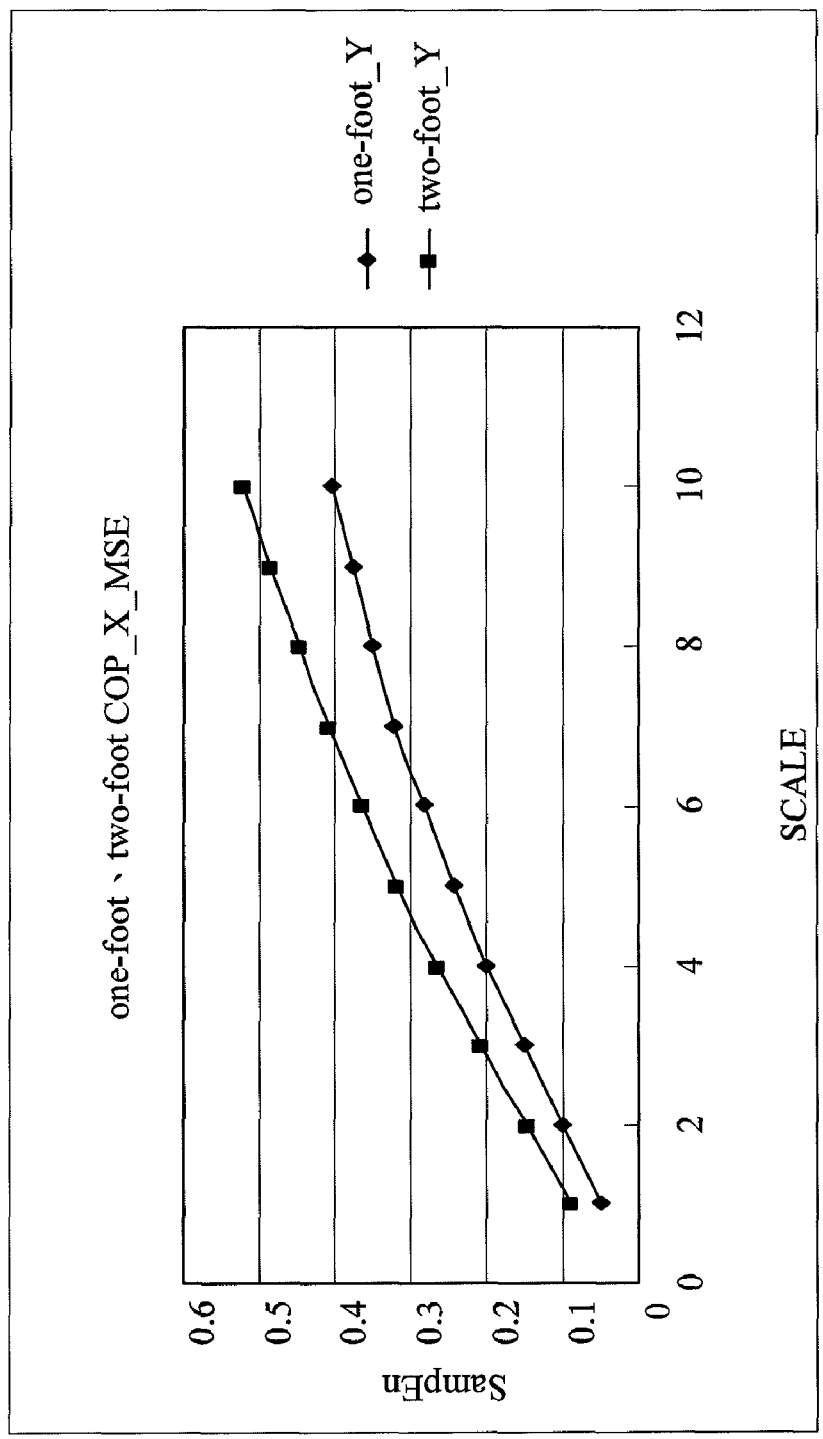
FIG. 17A shows the right-and-left direction (X) COP position MSE curve when standing on one foot and two feet of the present invention.
Figure 17B:
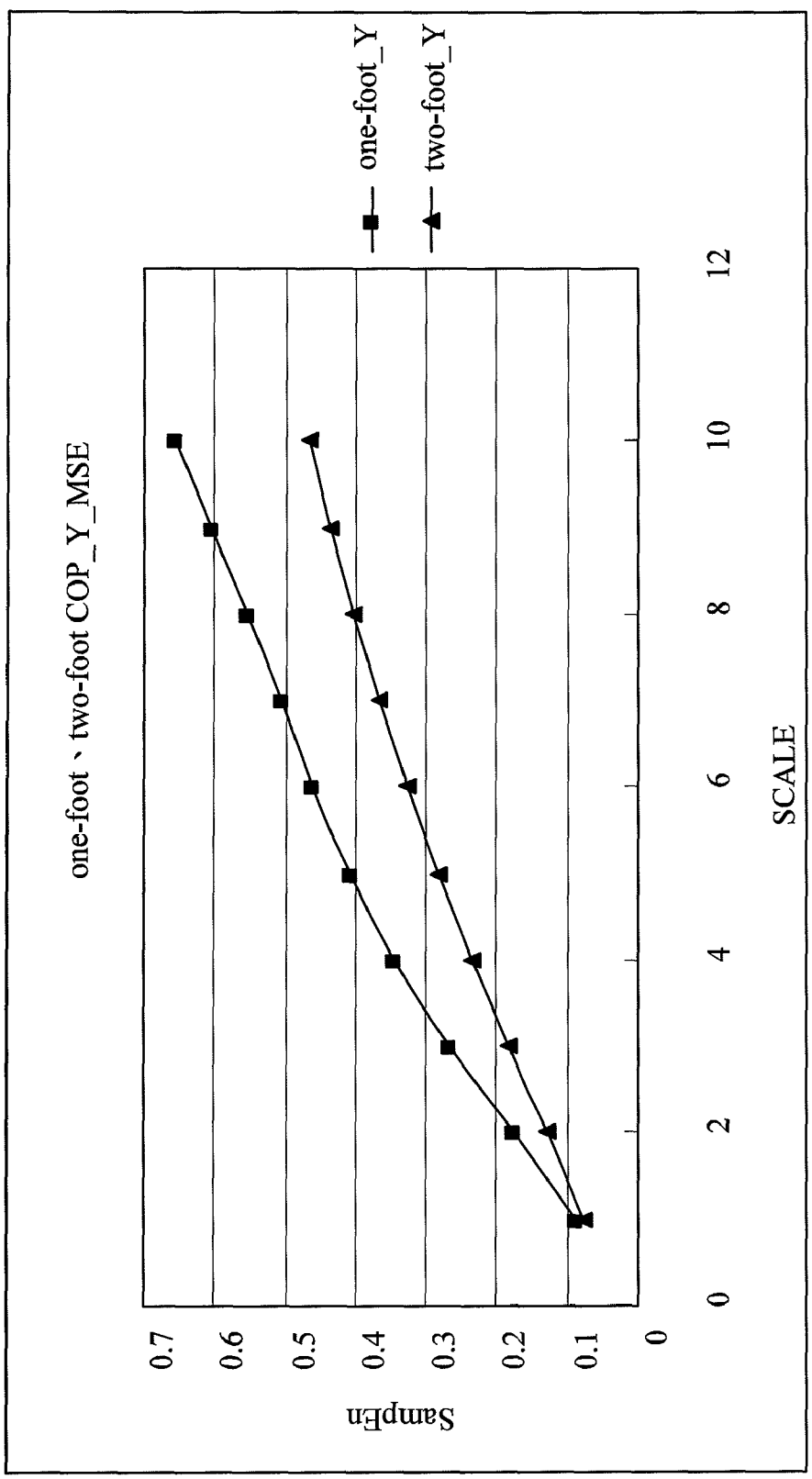
FIG. 17B shows the back-and-forth direction (Y) COP position MSE curve when standing on one foot and two feet of the present invention.
Figure 18A:
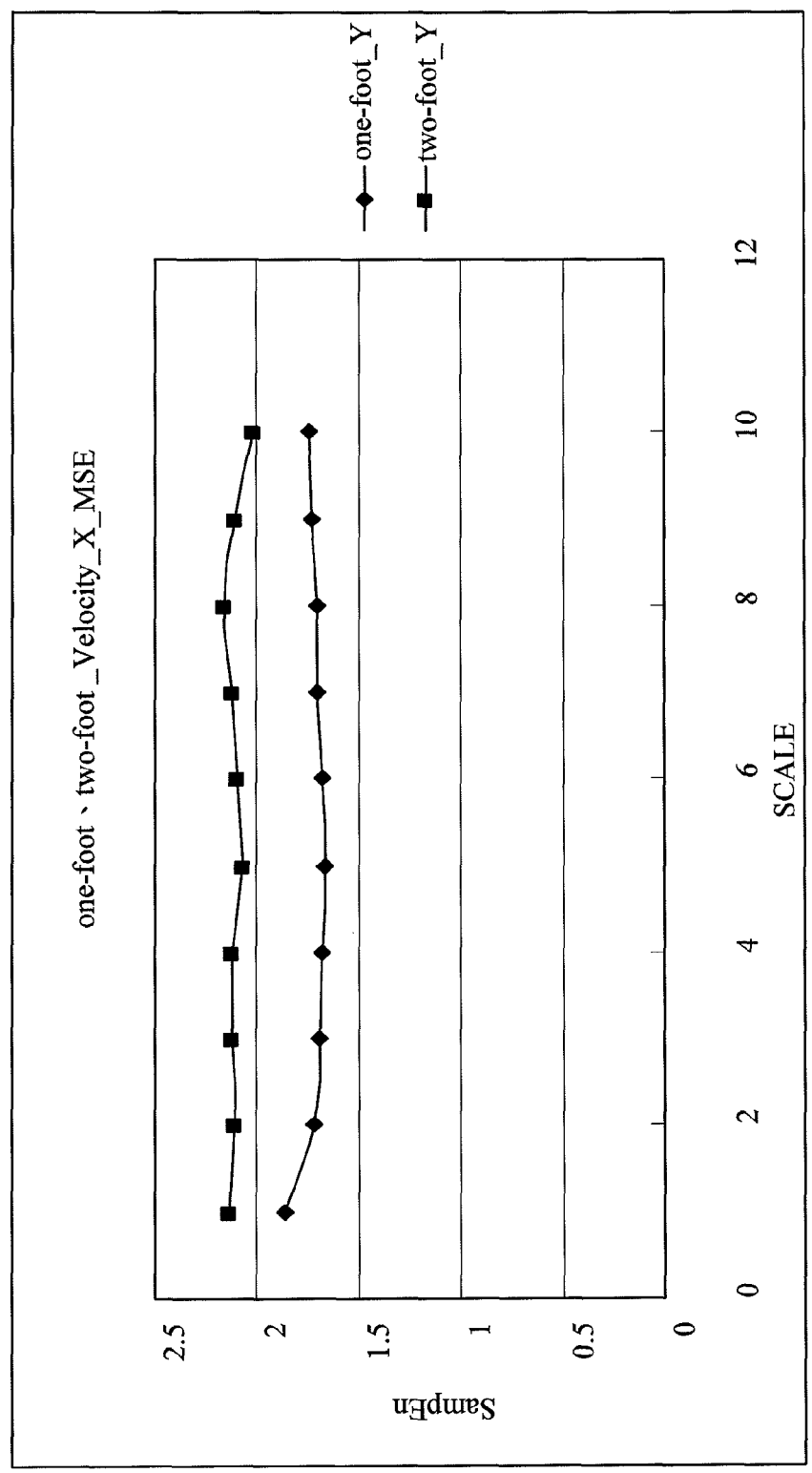
FIG. 18A shows the right-and-left direction (X) COP offset velocity MSE curve when standing on one foot and two feet of the present invention.
Figure 18B:
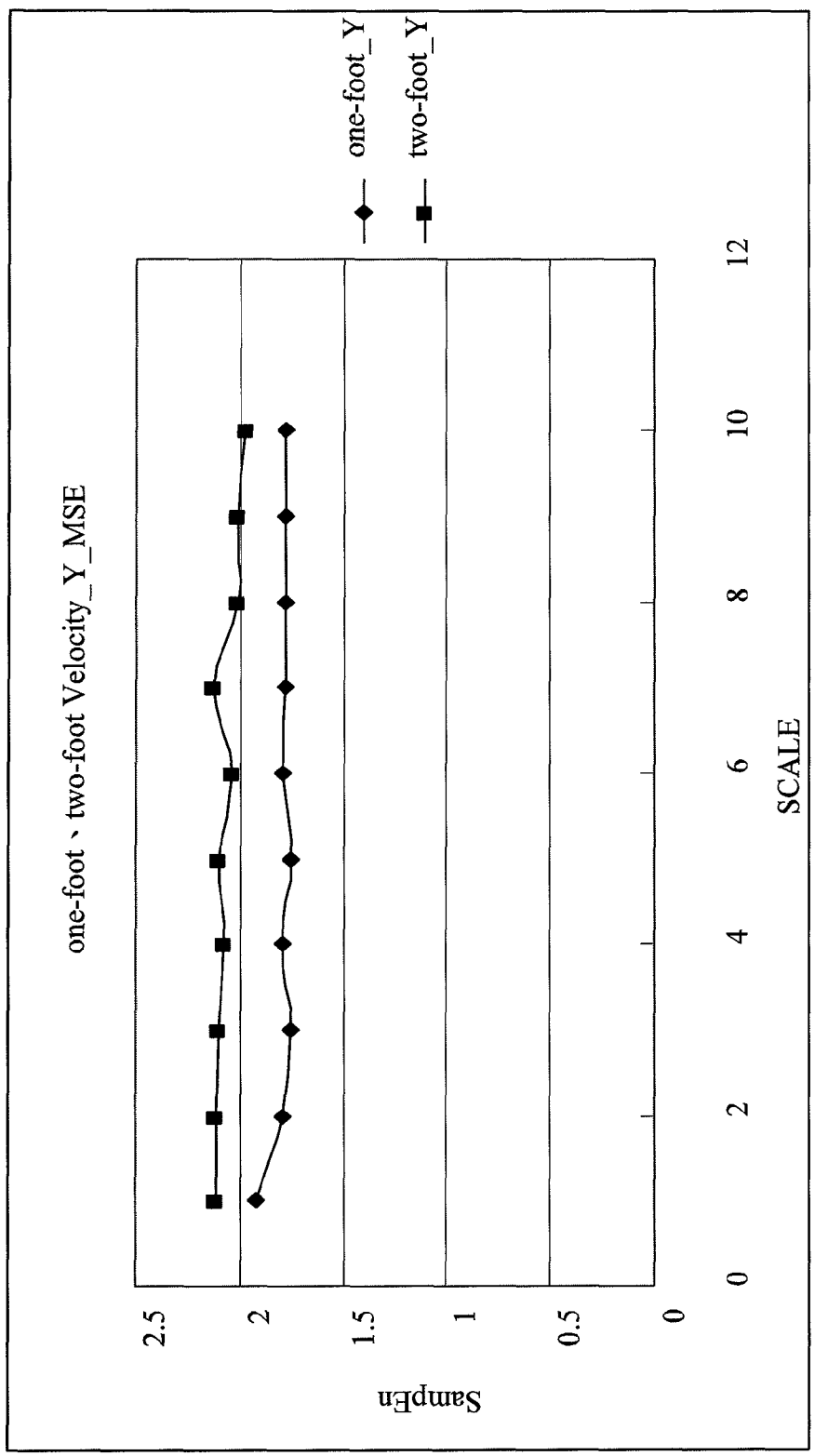
FIG. 18B shows the back-and-forth direction (Y) COP offset velocity MSE curve when standing on one foot and two feet of the present invention.

The results shown in the above Table 2 show the system can distinguish the differences among the three types of signals. The system noise has the most entropy, the one-foot balance status is not as stable as two-feet so the subjects will continue to change the COP position to maintain balance. The two-foot balance status has more stability so the test subjects do not change the COP position as often. Therefore, as seen in FIGS. 17A and 17B, the complexity of the balance signals for standing on one foot is greater than the complexity of the balance signals for standing on two feet. As for the $C_I$ value, as shown in FIGS. 18A and 18B, the two feet situation has the greater value than the one foot situation.

Figure 19:
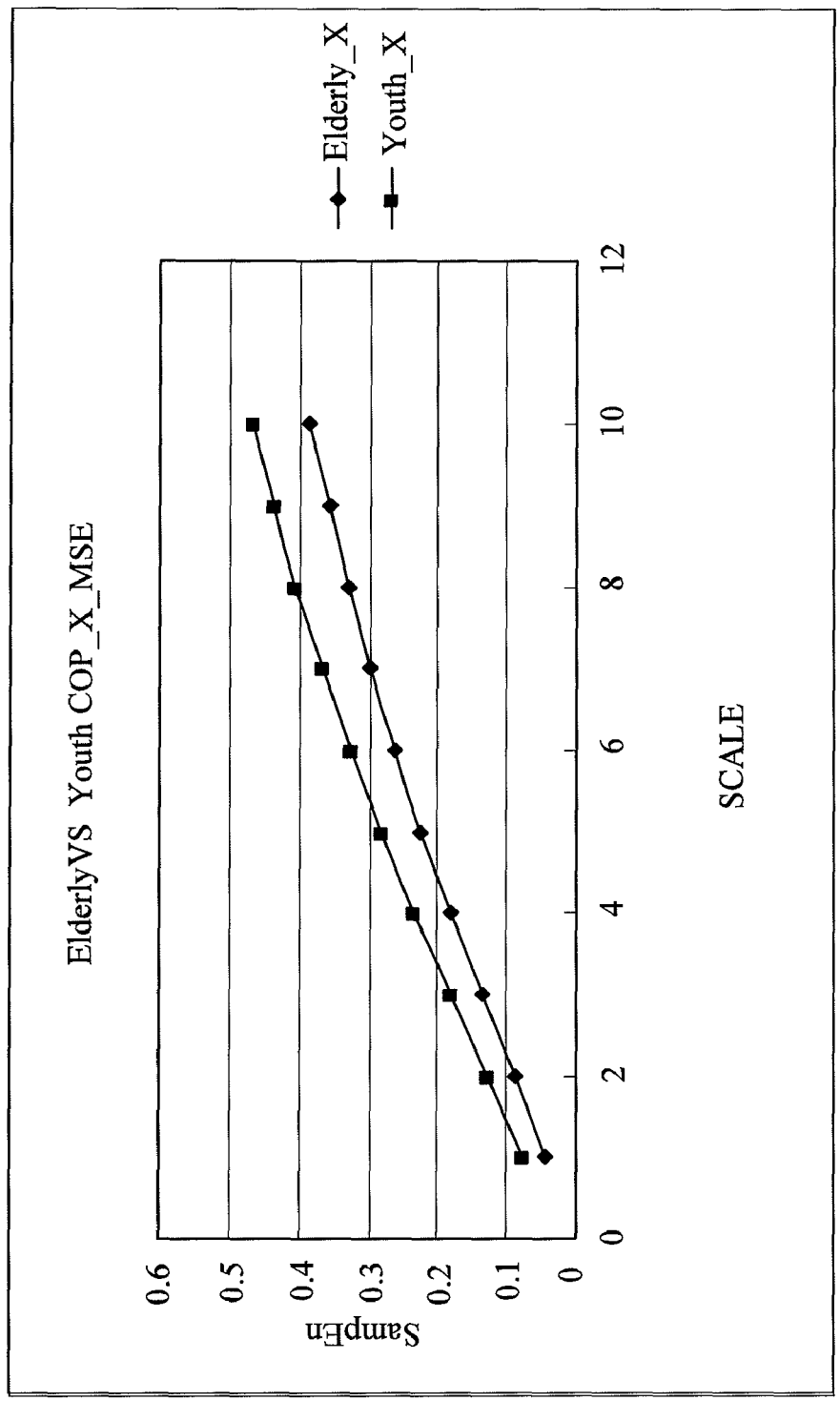
FIG. 19 shows the right-and-left direction (X) COP position offset MSE curve for elderly and youth of the present invention.
Figure 20:
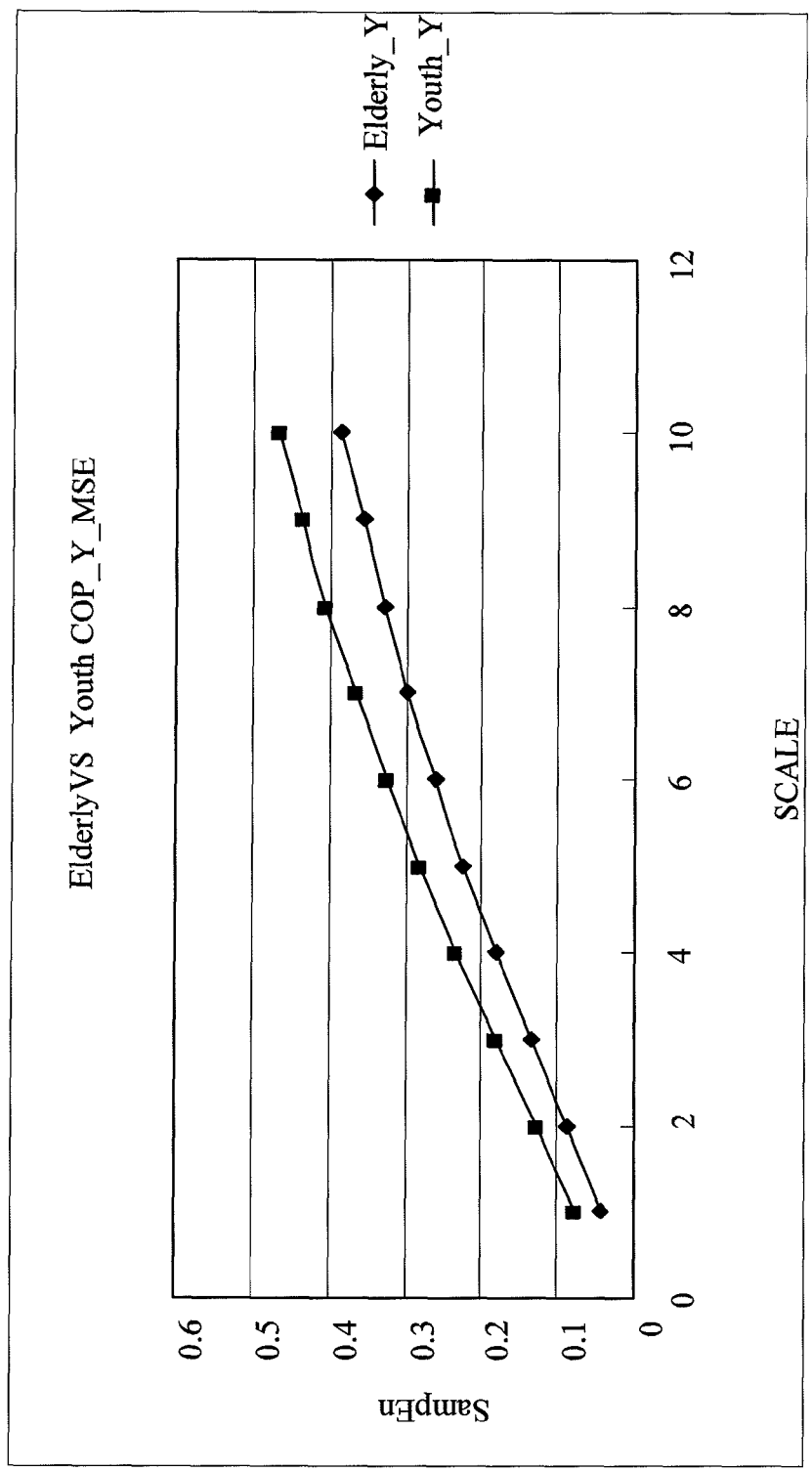
FIG. 20 shows the back-and-forth direction (Y) COP position offset MSE curve for elderly and youth of the present invention.

In FIGS. 19 and 20, the right-and-left direction (X) COP position of offset MSE curve and the back-and-forth direction (Y) COP position of offset MSE curve for elderly and youth of this invention is shown. This practical example measures the body balance signals for the elderly and the youth and also has the MSE analysis for center of weight position offset and offset velocity. The elderly are aged between 65 and 84 years old and the youth are between 20 and 28. From FIG. 19, where COP_X_MSE represents the center of weight position MSE curve for the elderly and the youth in the left-and-right direction, the center of weight position MSE curve of the elderly is lower than that of the youth. From FIG. 20, where COP_Y_MSE represents the center of weight position MSE curve for the elderly and the youth in the back-and-forth direction, the center of weight position MSE curve of the elderly is also lower than that of the youth. So as to know in the center of weight MSE analysis, both the left-and-right direction and the back-and-forth direction, the MSE value of the elderly is lower than that of the youth.

Figure 21:
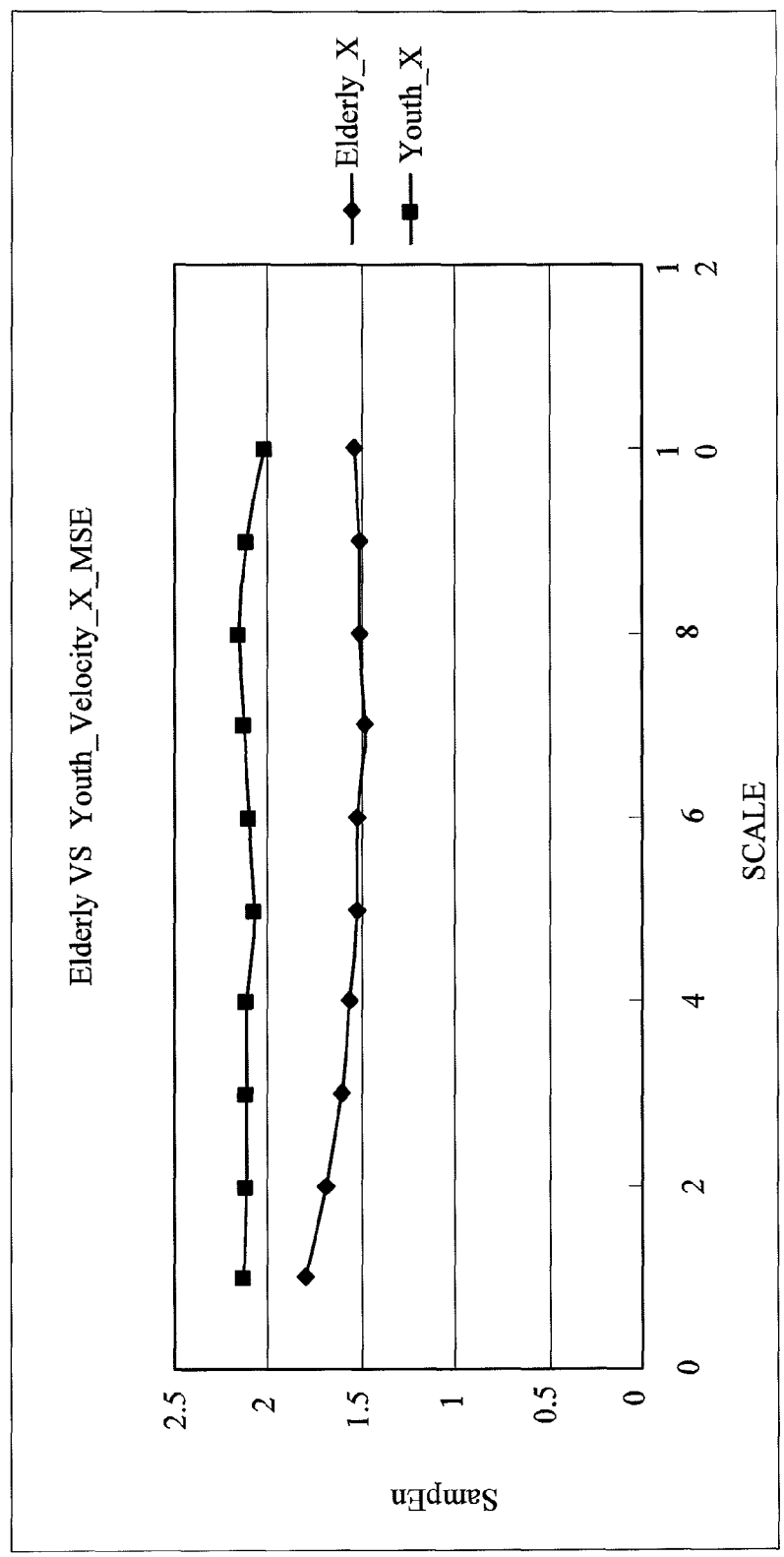
FIG. 21 shows the right-and-left direction (X) COP offset velocity MSE curve for elderly and youth of the present invention.
Figure 22:
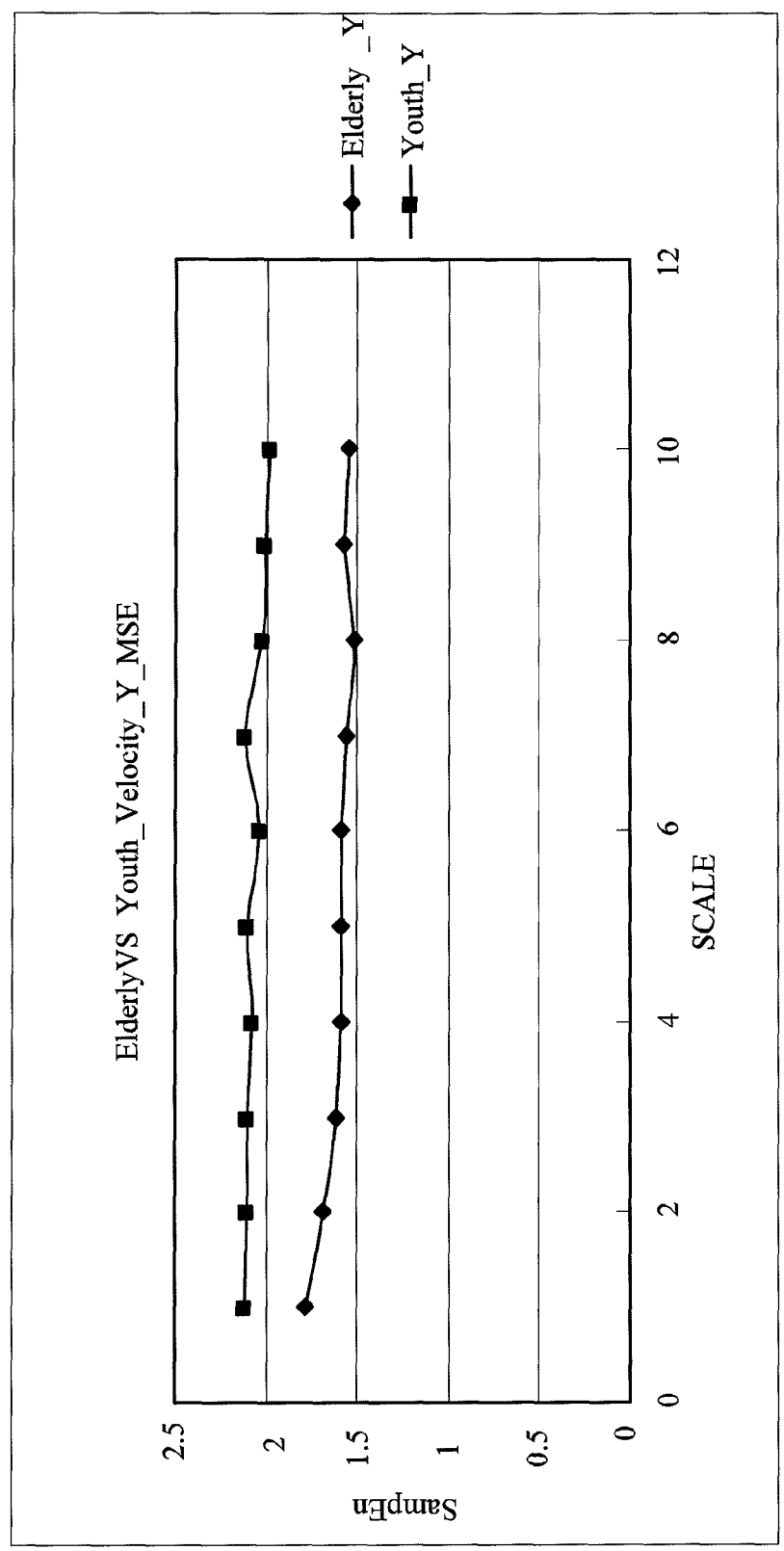
FIG. 22 shows the back-and-forth direction (Y) COP offset velocity MSE curve for elderly and youth of the present invention.

In FIG. 21 and FIG. 22 the right-and-left direction (X) and the back-and-forth direction (Y) COP offset velocity MSE curve for elderly and youth of this invention are shown. From FIG. 21, where Velocity_X_MSE represents the offset velocity MSE curve for the elderly and the youth in the left-and-right direction, the offset velocity MSE curve of the elderly is lower than that of the youth. From FIG. 22, where Velocity_Y_MSE represents the offset velocity MSE curve for the elderly and the youth in the back-and-forth direction, the offset velocity MSE curve of the elderly is also lower than that of the youth. So it is known in the offset velocity MSE analysis, both the left-and-right direction and the back-and-forth direction, the MSE value of the elderly is lower than that of the youth.

Table 3 shows the $C_I$ analysis result for COP position and COP offset velocity for the elderly and the youth presented in the format of average±standard variation. The P values from t-test analysis in statistics are used to represent the variety thereof.

Table 3 has the following 4 results:

The $C_I$ for the elderly in the left-and-right direction COP position has an average of 2.48 which is lower than the average of 3.25 for the youth.

The $C_I$ for the elderly in the back-and-forth direction COP position has an average of 2.30 which is lower than the average of 2.89 for the youth.

The $C_I$ for the elderly in the left-and-right direction COP offset velocity has an average of 15.77 which is lower than the average of 21.06 for the youth.

The $C_I$ for the elderly in the back-and-forth direction COP offset velocity has an average of 16.05 which is lower than the average of 20.68 for the youth.

Comparing the signal analysis results from the elderly and the youth, the P values from t-test statistic analysis for the $C_I$'s of COP position in the left-and-right and back-and-right directions and COP offset velocity in the left-and-right and back-and-right directions are 0.068, 0.018, $3.773 \times 10^{-3}$, and $5.888 \times 10^{-4}$ separately. Except the one for COP position in the left-and-right direction is greater than 0.05, all the others are less than 0.05. Among these four comparisons, three of them have distinct difference; therefore this invention can distinguish the difference in complexity for the elderly and the youth.

The body balance signals measuring system and the analysis method provided in this invention has the following benefits compared to the prior art:

1. This invention of body balance signals measuring system and the analysis method provides a system capable of analyzing the sense of balance to collect and analyze the body balance data and to discover and prevent falling from happening.

2. This invention provides a sense of balance measuring device whose cost and operation method are affordable and not complicated for most people so they will not reject using this device.

3. This invention can be used in daily living or at home anytime and adjust the therapy objectives. Not only can the invention result in better treatment but it can also maintain and adjust the treatment more effectively.

The aforementioned descriptions are solely for explaining the embodiments of the present invention and are not intended to limit the scope of the present invention. Any equivalent practice of modification within the spirit of the present invention should be treated as being within the scope of patent of the present invention.

What is claimed is:
1. A body balance signals measuring system comprising:
 a measuring device that is linked with a filter amplifier, the measuring device captures voltage signals for pressure change and;

the filter amplifier that is connected to the measuring device and to an A/D convertor receiving the voltage signals from the measuring device and filters and amplifying the voltage signals collected by the measuring device and sending the signals to the A/D convertor;

the A/D convertor interfaced with the filter amplifier converts the voltage signals processed by the filter amplifier into digital signals;

a signal receiving module that is connected to the A/D convertor, the signal receiving module receives the digital signals from the A/D converter, the signal receiving module also stores the digital signal outputs from the A/D convertor; and a data analysis module that is connected to the signal receiving module, the data analysis module receives the digital signals from the signal receiving module to analyze voltage variations of the digital signals) to measure human body center of weight offsets, COP (center of pressure) position offsets, and COP offset velocities.

2. The body balance signals measuring system claimed in claim 1, wherein the measuring device has four weight sensors and one signal converting circuit where the weight sensors are configured to be replaced by electronic weight scales and the signal converting circuit is configured to gain the voltage signals caused by pressure changes.

3. The body balance signals measuring system claimed in claim 2, wherein the signal converting circuit uses a Wheatstone bridge circuit to collect the voltage signals, the Wheatstone bridge circuit has three types of gauges which include four active full bridge gauges, two half bridge gauges), and a single quarter bridge gauge.

4. The body balance signals measuring system claimed in claim 1, wherein the filter amplifier comprises a filter circuit and an amplify circuit, the filter circuit is configured to be either analog or digital and the amplify circuit is used to amplify the bridge circuit output voltage signals.

5. The body balance signals measuring system claimed in claim 1, wherein the signal receiving module is a signal receiving interface programmed with programming language and is configured to store the received signals for analysis.

6. The body balance signals measuring system claimed in claim 1, wherein the A/D convertor is configured to be replaced with an embedded system that is configured to catch the digital signals from the measuring device, convert the signals, analyze the data, and display results.

7. The body balance signals measuring system claimed in claim 1, wherein the data analysis module uses MSE (multiscale entropy) and other non-linear analysis method to extract data.

8. The body balance signals measuring system claimed in claim 1, wherein the data analysis module uses COP position offsets and COP offset velocities for MSE curve and MSE curve complexity analysis.

9. A body balance signals measuring and analysis method comprising:
1) obtaining and analyzing center-of-weight offset voltage signals using measuring devices, filter amplifier, A/D convertor, and signal receiving module;
2) obtaining COP (center of pressure) position offset with data analysis module and processing the voltage signals collected by the measuring device for center of weight offset, wherein the COP position offset is gained by COP analysis for COP position;
3) performing COP offset velocity analysis;
4) performing MSE (multiscale entropy) curve analysis; and
5) performing MSE curve complexity analysis.

10. The body balance signals measuring and analysis method as claimed in claim 9, wherein the center-of-weight offset voltage signals are retrieved by body weight loaded voltages in four sensors in the measuring devices subtracted from base voltages of each of the four sensors.

11. The body balance signals measuring and analysis method as claimed in claim 10, wherein the COP position offset analysis uses counter forces on the four sensors when loaded with weight in conjunction with distances between the four sensors to analyze for COP in left-and-right and back-and-forth directions.

12. The body balance signals measuring and analysis method as claimed in claim 11, wherein the COP offset velocity analysis is subtracted from a last sampled COP position value from the COP position for being divided by sample time to retrieve the COP offset velocity, in which the COP off set velocity has left-and-right and back-and-forth directions.

13. The body balance signals measuring and analysis method as claimed in claim 9, wherein the MSE curve complexity is an area beneath an MSE curve used to analyze MSE curve complexity.

* * * * *